(12) United States Patent
Shreim et al.

(10) Patent No.: US 11,534,110 B2
(45) Date of Patent: *Dec. 27, 2022

(54) NOSE SENSOR

(71) Applicant: MASIMO CORPORATION, Irvine, CA (US)

(72) Inventors: Samir Shreim, Irvine, CA (US); Vikrant Sharma, Santa Ana, CA (US); Philip Perea, Irvine, CA (US); Jennifer Rines, Carlsbad, CA (US); Clinton Robins, Lake Forest, CA (US); Chad Eichele, Lake Forest, CA (US); Yassir Kamel Abdul-Hafiz, Irvine, CA (US); Sean Devlin, Irvine, CA (US)

(73) Assignee: MASIMO CORPORATION, Irvine, CA (US)

( * ) Notice: Subject to any disclaimer, the term of this patent is extended or adjusted under 35 U.S.C. 154(b) by 223 days.

This patent is subject to a terminal disclaimer.

(21) Appl. No.: 17/079,028

(22) Filed: Oct. 23, 2020

(65) Prior Publication Data

US 2021/0169418 A1 Jun. 10, 2021

Related U.S. Application Data

(63) Continuation of application No. 15/955,500, filed on Apr. 17, 2018, now Pat. No. 10,849,554.
(Continued)

(51) Int. Cl.
*A61B 5/1455* (2006.01)
*A61B 5/024* (2006.01)
(Continued)

(52) U.S. Cl.
CPC .......... *A61B 5/6819* (2013.01); *A61B 5/0015* (2013.01); *A61B 5/02438* (2013.01); *A61B 5/14552* (2013.01); *A61B 5/0205* (2013.01)

(58) Field of Classification Search
CPC ..... A61B 5/1455; A61B 5/14552; A61B 5/68; A61B 5/6819; A61B 5/02438
See application file for complete search history.

(56) References Cited

U.S. PATENT DOCUMENTS

| 4,543,146 A | 9/1985 | Petcen |
|---|---|---|
| 4,685,464 A | 8/1987 | Goldberger et al. |

(Continued)

FOREIGN PATENT DOCUMENTS

| WO | WO 93/005710 | 4/1993 |
|---|---|---|
| WO | WO 96/013208 | 5/1996 |

(Continued)

OTHER PUBLICATIONS

US 2022/0192529 A1, 06/2022, Al-Ali et al. (withdrawn)
(Continued)

*Primary Examiner* — Eric F Winakur
(74) *Attorney, Agent, or Firm* — Knobbe, Martens, Olson & Bear, LLP

(57) ABSTRACT

A patient monitor can noninvasively measure a physiological parameter using sensor data from a nose sensor configured to be secured to a nose of the patient. The nose sensor can include an emitter and a detector. The detector is configured to generate a signal when detecting light attenuated by the nose tissue of the patient. An output measurement of the physiological parameter can be determined based on the signals generated by the detector. The nose sensor can include an inner prong and an outer prong to assist the nose sensor in securing to a patient's nose. The detector can be coupled to an inner post of the inner prong and can be configured to secure to an interior or exterior portion of the patient's nose.

14 Claims, 23 Drawing Sheets

Related U.S. Application Data

(60) Provisional application No. 62/486,886, filed on Apr. 18, 2017.

(51) Int. Cl.
*A61B 5/0205* (2006.01)
*A61B 5/00* (2006.01)

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Hink et al. |
| 5,163,438 A | 11/1992 | Gordon et al. |
| 5,190,048 A | 3/1993 | Wilkinson |
| 5,247,931 A | 9/1993 | Norwood |
| 5,319,355 A | 6/1994 | Russek |
| 5,335,659 A | 8/1994 | Pologe |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| 5,383,469 A | 1/1995 | Vreman et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,724 A | 9/1998 | Gronvall |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,621 A | 9/2000 | Chin |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,535,714 B2 | 3/2003 | Melker et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |

(56) References Cited

U.S. PATENT DOCUMENTS

| | | |
|---|---|---|
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,909,912 B2 | 6/2005 | Melker |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,024,235 B2 | 4/2006 | Melker et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,127,278 B2 | 10/2006 | Melker et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,313,425 B2 | 12/2007 | Finarov et al. |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |

(56) References Cited

U.S. PATENT DOCUMENTS

| | | |
|---|---|---|
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,785,262 B2 | 8/2010 | Melker et al. |
| 7,791,155 B2 | 9/2010 | Diab |
| 7,801,581 B2 | 9/2010 | Diab |
| 7,820,108 B2 | 10/2010 | Lampotang et al. |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,887,502 B2 | 2/2011 | Ross et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,460 B2 | 3/2011 | Melker et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,073,518 B2 | 12/2011 | Chin |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,211,035 B2 | 7/2012 | Melker et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,279,063 B2 | 10/2012 | Wohltjen |
| 8,280,473 B2 | 10/2012 | Al-Ali |
| 8,281,787 B2 | 10/2012 | Burton |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,444,570 B2 | 5/2013 | McGonigle et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,525,666 B2 | 9/2013 | Melker et al. |
| 8,529,301 B2 | 9/2013 | Al-Ali et al. |
| 8,529,459 B2 | 9/2013 | Malker et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |

(56) References Cited

U.S. PATENT DOCUMENTS

| | | |
|---|---|---|
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,641,635 B2 | 2/2014 | Melker et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,679,028 B2 | 3/2014 | Melker et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,740,808 B2 | 6/2014 | Curti et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,857 B2 | 6/2014 | Melker et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,801,620 B2 | 8/2014 | Melker et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| D717,192 S | 11/2014 | Tanner et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,897,850 B2 | 11/2014 | Jochim et al. |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,155,826 B2 | 10/2015 | Ross et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,198,586 B2 | 12/2015 | Melker |
| 9,211,072 B2 | 12/2015 | Kiani |
| 9,211,095 B1 | 12/2015 | Al-Ali |
| 9,218,454 B2 | 12/2015 | Kiani et al. |
| D748,274 S | 1/2016 | Rich et al. |
| 9,226,696 B2 | 1/2016 | Kiani |
| 9,241,662 B2 | 1/2016 | Al-Ali et al. |
| 9,245,668 B1 | 1/2016 | Vo et al. |
| D748,774 S | 2/2016 | Caron |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,370,634 B2 | 6/2016 | Melker et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |

(56) References Cited

U.S. PATENT DOCUMENTS

| | | |
|---|---|---|
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,661 B2 | 6/2017 | Melker et al. |
| 9,668,679 B2 | 6/2017 | Schurman et al. |
| 9,668,680 B2 | 6/2017 | Bruinsma et al. |
| 9,668,695 B2 | 6/2017 | Melker |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,717,836 B2 | 8/2017 | Melker |
| 9,724,002 B2 | 8/2017 | Rich et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| D802,152 S | 11/2017 | Wakefield et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,950,112 B2 | 4/2018 | Melker et al. |
| 9,955,937 B2 | 5/2018 | Telfort |
| 9,965,946 B2 | 5/2018 | Al-Ali et al. |
| 9,974,479 B2 | 5/2018 | Melker |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| D844,793 S | 4/2019 | Dai |
| 10,279,247 B2 | 5/2019 | Kiani |
| 10,292,664 B2 | 5/2019 | Al-Ali |
| 10,299,720 B2 | 5/2019 | Brown et al. |
| 10,307,111 B2 | 6/2019 | Muhsin et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,390,715 B2 | 8/2019 | Rich et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |

(56) References Cited

U.S. PATENT DOCUMENTS

| | | |
|---|---|---|
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D957,648 S | 7/2022 | Al-Ali |
| 11,389,093 B2 | 7/2022 | Triman et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2004/0230108 A1 | 11/2004 | Melker et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0078315 A1 | 4/2007 | Kling et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0092898 A1 | 4/2008 | Schneider et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0085527 A1 | 4/2010 | Konuma et al. |
| 2010/0085537 A1 | 4/2010 | Ramella-Roman et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0227740 A1 | 9/2011 | Wohltjen |
| 2011/0230733 A1 | 9/2011 | Al-Ali |
| 2011/0237969 A1 | 9/2011 | Eckerbom et al. |
| 2012/0078069 A1 | 3/2012 | Melker |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0272963 A1 | 11/2012 | Thomas et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0005557 A1 | 1/2014 | Rich et al. |
| 2014/0012100 A1 | 1/2014 | Al-Ali et al. |
| 2014/0051953 A1 | 2/2014 | Lamego et al. |
| 2014/0081100 A1 | 3/2014 | Muhsin et al. |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275887 A1 | 9/2014 | Batchelder et al. |
| 2014/0275930 A1 | 9/2014 | Rich et al. |
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |

(56) References Cited

U.S. PATENT DOCUMENTS

| | | |
|---|---|---|
| 2014/0343382 A1 | 11/2014 | Kersey et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0073233 A1 | 3/2015 | Rich et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0105632 A1 | 4/2015 | Melker et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0297137 A1 | 10/2015 | Welch et al. |
| 2015/0342480 A1 | 12/2015 | Justice et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366507 A1 | 12/2015 | Blank et al. |
| 2015/0380875 A1 | 12/2015 | Coverston et al. |
| 2016/0029932 A1 | 2/2016 | Al-Ali |
| 2016/0051205 A1 | 2/2016 | Al-Ali et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0174855 A1 | 6/2016 | Deliwala |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224231 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0258403 A1 | 9/2017 | Abdul-Hafiz et al. |
| 2017/0311891 A1 | 11/2017 | Kiani et al. |
| 2018/0103874 A1 | 4/2018 | Lee et al. |
| 2018/0153446 A1 | 6/2018 | Kiani |
| 2018/0199871 A1 | 7/2018 | Pauley et al. |
| 2018/0213583 A1 | 7/2018 | Al-Ali |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |

(56) References Cited

U.S. PATENT DOCUMENTS

| | | |
|---|---|---|
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |

FOREIGN PATENT DOCUMENTS

| | | |
|---|---|---|
| WO | WO 2005/065540 | 7/2005 |
| WO | WO 2018/194992 | 10/2018 |

OTHER PUBLICATIONS

International Search Report and Written Opinion received in PCT Application No. PCT/US2018/027833, dated Jul. 5, 2018.

International Preliminary Report on Patentability and Written Opinion received in PCT Application No. PCT/US2018/027833, dated Oct. 31, 2019.

U.S. Appl. No. 15/955,500, Nose Sensor, filed Apr. 17, 2018, U.S. Pat. No. 10,849,554.

NOSE SENSOR

INCORPORATION BY REFERENCE TO ANY PRIORITY APPLICATIONS

This application is a continuation of U.S. patent application Ser. No. 15/955,500, filed Apr. 17, 2018, titled NOSE SENSOR, which claims the benefit of the U.S. Provisional Application No. 62/486,886, filed Apr. 18, 2017, titled NOSE SENSOR. The entire contents of the above-identified patent applications are incorporated by reference herein and made a part of this specification.

TECHNICAL FIELD

In general, the present disclosure relates to a wearable patient monitoring device, and methods and apparatuses for monitoring a patient's physiological information using the device. More specifically, the present disclosure relates to the connection of a patient monitoring device to a patient's nose.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters such as blood oxygen saturation level, respiratory rate, pulse, and a myriad of other parameters, such as those monitored on commercially available patient monitors from Masimo Corporation of Irvine, Calif. Clinicians, including doctors, nurses, and other medical personnel, use the physiological parameters and trends of those parameters obtained from patient monitors to diagnose illnesses and to prescribe treatments. Clinicians also use the physiological parameters to monitor patients during various clinical situations to determine whether to increase the level of medical care given to patients.

Examples of non-invasive patient monitoring devices include pulse oximeters. Pulse oximetry is a widely accepted noninvasive procedure for measuring the oxygen saturation level of arterial blood, an indicator of a person's oxygen supply. A pulse oximeter generally includes one or more light sources transmitting optical radiation into or reflecting off through a portion of the body, for example a digit such as a finger, a hand, a foot, a nose, an earlobe, or a forehead. The one or more light sources can emit radiation at a plurality of wavelengths including, one, two, four, eight, twelve, sixteen or more different wavelengths, or any number therebetween. After attenuation of the radiation by tissue and fluids of the portion of the body, one or more photodetection devices detect the attenuated light and output one or more detector signals responsive to the detected attenuated light. The oximeter may calculate oxygen saturation ($SpO_2$), pulse rate, a plethysmograph waveform, perfusion index (PI), pleth variability index (PVI), methemoglobin (HbMet), carboxyhemoglobin (HbCO), total hemoglobin (HbT), glucose, and/or otherwise, and the oximeter may display on one or more monitors the foregoing parameters individually, in groups, in trends, as combinations, or as an overall wellness or other index. An example of such an oximeter, which can utilize an optical sensor described herein, are described in U.S. application Ser. No. 13/762,270, filed Feb. 7, 2013, titled "Wireless Patient Monitoring Device," U.S. application Ser. No. 14/834,169, filed Aug. 24, 2015, titled "Wireless Patient Monitoring Device," and U.S. application Ser. No. 14/511,974, filed Oct. 10, 2014, titled "Patient Position Detection System," the disclosures of which are hereby incorporated by reference in their entirety. Other examples of such oximeters are described in U.S. application Ser. No. 09/323,176, filed May 27, 1999, titled "Stereo Pulse Oximeter," now U.S. Pat. No. 6,334,065, the disclosure of which is hereby incorporated by reference in its entirety.

In noninvasive devices and methods, a sensor is often adapted to position a portion of the body proximate the light source and light detector. In one example, noninvasive sensors often include a clothespin-shaped finger clip that includes a contoured bed conforming generally to the shape of a finger. An example of such a noninvasive sensor is described in U.S. application Ser. No. 12/829,352, filed Jul. 1, 2010, titled "Multi-Stream Data Collection System for Noninvasive Measurement of Blood Constituents," now U.S. Pat. No. 9,277,880, the disclosure of which is hereby incorporated by reference in its entirety. In another example, noninvasive sensors can include one or more sensing components, such as the light source and/or the photodetectors on an adhesive tape, such as described in U.S. application Ser. No. 13/041,803, filed May 7, 2011, titled "Reprocessing of a physiological sensor," now U.S. Pat. No. 8,584,345, the disclosure of which is hereby incorporated by reference in its entirety.

The patient monitoring devices can also communicate with an acoustic sensor comprising an acoustic transducer, such as a piezoelectric element. The acoustic sensor can detect respiratory and other biological sounds of a patient and provide signals reflecting these sounds to a patient monitor. An example of such an acoustic sensor, which can implement any of the acoustic sensing functions described herein, is described in U.S. application Ser. No. 12/643,939, filed Dec. 21, 2009, titled "Acoustic Sensor Assembly," now U.S. Pat. No. 8,771,204 and in U.S. application Ser. No. 61/313,645, filed Mar. 12, 2010, titled "Acoustic Respiratory Monitoring Sensor Having Multiple Sensing Elements," the disclosures of which are hereby incorporated by reference in their entirety. An example of such an acoustic sensor is also described in U.S. application Ser. Nos. 13/762,270, 14/834,169, and 14/511,974 referenced above.

SUMMARY

For purposes of summarizing the disclosure, certain aspects, advantages and novel features of several systems have been described herein. It is to be understood that not necessarily all examples of the present disclosure are disclosed herein. Thus, the systems disclosed herein can be embodied or carried out in a manner that achieves or optimizes one advantage or group of advantages as taught herein without necessarily achieving other advantages as can be taught or suggested herein.

A noninvasive physiological monitoring device can be configured secure to a nose of a patient. The device can include an inner prong configured to be positioned on one of an inner or outer side of a nose. The inner prong can include an inner post. The monitoring device can include an outer prong configured to be positioned on one of an inner or outer side of a nose. The outer prong can include a first outer post and a second outer post. The monitoring device can include a detector configured to be secured to one of an inner or outer wall of the nose of the patient. The monitoring device can include one or more light emitters configured to be secured to the other of the inner and outer wall of the nose of the patient. The monitoring device can include a coupling portion configured to space the inner prong from the outer prong, wherein the coupling portion provides support to the inner and outer prongs to secure the device to the nose of the patient. The first and second outer posts of the outer prong can be curved to conform to a portion of the nose of the patient. The inner prong can be curved to conform to a portion of the nose of the patient. The first outer post can have a first radius of curvature and a first curve direction, and the second outer post can have a second radius of curvature and a second curve direction, and the first radius of curvature can be equal to the second radius of curvature and the first curve direction can be the same as the second curve direction. The inner prong can be curved along a third radius of curvature and in a third direction, and the third radius of curvature can be equal to the first and second radius of curvatures and the third direction can be the same as the first and second curve directions. The outer prong of the monitoring device can be U-shaped. The inner prong can include an intermediate region and the outer prong can include an intermediate region. The intermediate region of the inner prong can be curved such that the intermediate region of the inner prong extends towards the intermediate region of the outer prong. The monitoring device can include an adhesive configured to adhere the emitter or the detector to an outer surface of the nose of the patient. The monitoring device can include a lens proximate to the detector configured to focus light into the detector. The lens can comprise a simple lens. The monitoring device can include a diffuser positioned proximate to the emitter and configured to diffuse light emitted by the emitter prior to entering tissue of the nose of the patient. The diffuser can comprise silicone. The inner post can be coupled to the detector. The inner post can be substantially rigid. The emitter can include a liner configured to cover the adhesive of the emitter when the emitter is not in use. The inner prong can include an inner base, and the outer prong further can include an outer base. The coupling portion can be circular. The monitoring device can include a first central longitudinal axis of the inner post that is aligned with a second central longitudinal axis of the inner prong, wherein the first outer post of the outer prong is spaced from the second outer post of the outer prong such that the first outer post has a first side wall that is positioned adjacent a second side wall of the outer prong and the second outer post has a third side wall that is positioned adjacent to a fourth side wall of the outer prong that is positioned opposite the second side wall of the outer prong. The monitoring device can include a first central longitudinal axis of the inner post is aligned with a second central longitudinal axis of the inner prong, wherein the inner post includes a first side wall and a second side wall, wherein the first outer post and the second outer post are spaced laterally away from one another along the outer prong such that the first outer post is positioned laterally outward from the first side wall of the inner post and the second outer post is positioned laterally outward from the second side wall of the inner post. The inner post can be configured to apply pressure to an inner portion of the nose of the patient, and the first outer post can be configured to apply pressure to a first outer portion of the nose of the patient that is spaced laterally outwardly from the inner portion of the patient's nose, and the second outer post can be configured to apply pressure to a second outer portion of the nose of the patient that is spaced laterally outwardly from the inner portion of the patient's nose. The inner post can be configured to apply pressure to a portion of the nose of the patient and the portion of the nose of the patient can be configured to be positioned between the first outer post and the second outer post when the inner prong and the outer prong are secured to the patient. The coupling portion can include the inner base and the outer base, wherein the inner base includes a top surface and the outer base includes a top surface. The inner post can extend from a center of the inner base. The first outer post can be spaced apart from the second outer post, and the first outer post and the second outer post can extend from the outer base. The inner post can be wider than the first outer post and the second outer post. The first prong can be parallel to the second prong. The coupling portion can comprise a joint configured to rotatably connect the inner prong and the outer prong, the joint including a first joint portion coupled to the inner prong and a second joint portion coupled to the outer prong, wherein the first joint portion has a first slot and the second joint portion has a second slot, the first slot and the second slot configured to at least partially receive a pin. The monitoring device can include a biasing member configured to bias the inner prong from the outer prong. The biasing member can comprise a spring. The monitoring device can include a diffuser positioned proximate to the emitter and configured to diffuse light emitted by the emitter prior to entering tissue of the nose of the patient, and a lens proximate to the detector configured to focus light into the detector.

A method of calculating a measurement of physiological parameters of a patient can include: transmitting light, by an emitter of a nose sensor, of at least first and second wavelengths through tissue of a nose of a patient to a detector; detecting, by the detector of the nose sensor, light attenuated by the tissue of the nose of the patient; generating an output signal, by the nose sensor, based on the light detected at the nose of the patient; and determining the measurement of the physiological parameters, by the nose sensor, based on the output signal. The nose sensor can include: an inner prong configured to be positioned on one of an inner or outer side of a nose, the inner prong including an inner post; an outer prong configured to be positioned on one of an inner or outer side of a nose, the outer prong including a first outer post and a second outer post wherein one of the detector or emitter is coupled to one of the inner or outer prongs, the detector configured to be secured to a wall of the nose of the patient. The nose sensor can include a coupling portion configured to space the inner prong from the outer prong, wherein the coupling portion provides support to the inner and outer prongs to secure the device to the nose of the patient. The nose sensor can further include a diffuser and the method can further comprise diffusing the light transmitted by the emitter of the nose sensor prior to entering the tissue of the nose of the patient. The nose sensor can further include a lens and the method can further comprise focusing the light transmitted by the emitter of the nose sensor into the detector after the light has passed through the tissue of the nose of the patient. The inner prong can include an intermediate region and the outer prong can include an intermediate region. The intermediate region of the inner prong can be curved such that the intermediate region of the inner prong extends towards the intermediate region of the outer prong. The method can include using an adhesive to adhere either the emitter or detector to the nose of the patient, wherein the adhesive is configured to adhere to an outer surface of the nose of the patient. The method can include removing a liner from the adhesive before adhering either the emitter or detector to the nose of the patient. The first and second outer posts of the outer prong can be curved to conform to the nose of the patient. The first outer post can have a first radius of curvature and a first curve direction, and the second outer post can have a second radius of curvature and a second curve direction, the first radius of curvature being equal to the second radius of curvature and the first curve direction being the same as the second curve direction. The inner prong can be curved along a third radius of curvature and in a third direction, wherein the third radius of curvature is equal to the first and second radius of curvatures and the third direction is the same as the first and second curve directions. The coupling portion can include a joint configured to rotatably connect the inner prong and the outer prong, the joint including a first joint portion coupled to the inner prong and a second joint portion coupled to the outer prong, wherein the first joint portion has a first slot and the second joint portion has a second slot, the first slot and the second slot configured to at least partially receive a pin. The method can include biasing the inner prong from the outer prong with a biasing member. The biasing member can comprise a spring. The detector of the nose sensor can be coupled to the inner post of the inner prong and configured to be secured to an inner wall of the patient's nose. The detector can be coupled to a first end of a flexible circuit and the emitter can be coupled to a second end of the flexible circuit, wherein the method further comprises adhering the emitter to an outer wall of the patient's nose. The first and second outer posts of the outer prong can have a substantially similar radius of curvature and curve in the same direction, thereby permitting the outer prong to conform to a portion of the nose of the patient. The inner prong can be curved along a second radius of curvature and in a second direction substantially similar to the radius of curvature and curve direction of the first and second outer posts of the outer prong. The outer prong can be U-shaped.

A noninvasive physiological monitoring device configured to secure to a nose of a patient can include an emitter configured to emit light through the nose of the patient towards a detector, wherein the detector is configured to detect light attenuated through the nose of the patient. The emitter can be configured to emit light of at least a first and second wavelength. The monitoring device can include an adhesive configured to adhere the emitter to an outer surface of the nose of the patient. The monitoring device can include a liner configured to cover the adhesive of the emitter when the emitter is not in use. The monitoring device can include a lens configured to focus light into the detector. The lens can comprise glass, plastic, or both glass and plastic. The lens can comprise a simple lens. The lens can comprise one layer of material selected from the group consisting of glass and plastic. The lens can comprise at least two layers. The at least two layers can comprise a material selected from the group consisting of glass and plastic. The lens can comprise two or more simple lenses arranged about a common axis. The monitoring device can include a diffuser configured to diffuse light emitted by the emitter prior to entering tissue of the nose of the patient. The diffuser can be is located proximate to the emitter. The diffuser can comprise silicone. The diffuser can comprise white silicone, or alternatively, black silicon. The diffuser can comprise acrylic, plastic, and/or glass. The diffuser can comprise two or more layers. Each of the two or more layers can comprise a different material, or alternatively, the same material or materials. The monitoring device can include a transmitter configured to transmit an output signal from the detector. The transmitter can comprise a cable configured to connect the noninvasive physiological monitoring device to at least one of a monitor or a display. The transmitter can comprise a wireless transmitter. The wireless transmitter can be configured to operate on a protocol selected from the group consisting of Wi-Fi, Bluetooth, ZigBee, Z-wave, radio frequency, cellular telephony, infrared, and satellite transmission. The monitoring device can include: an inner prong configured to be positioned on one of an inner or outer side of a nose; and an outer prong configured to be positioned on one of an inner or outer side of a nose, wherein the detector is coupled to one of the inner or outer prongs and configured to be secured to one of the inner or outer side of the nose. The inner prong can be parallel, non-parallel, or perpendicular to the outer prong. The emitter can be coupled to a first end of a flexible circuit and the detector can be coupled to a second end of the flexible circuit, and wherein a first portion of the flexible circuit is contained within the noninvasive physiological monitoring device and a second portion of the flexible circuit is not contained within the noninvasive physiological monitoring device, wherein the second portion is closer to the first end of the flexible circuit than to the second end. The inner prong can include an inner post and the outer prong can include a first outer post and a second outer post. The monitoring device can include a first central longitudinal axis of the inner post aligned with a second central longitudinal axis of the inner prong, wherein the first outer post of the outer prong is spaced from the second outer post of the outer prong such that the first outer post has a first side wall that is positioned adjacent a second side wall of the outer prong and the second outer post has a third side wall that is positioned adjacent to a fourth side wall of the outer prong that is positioned opposite the second side wall of the outer prong. The monitoring device can include a first central longitudinal axis of the inner post aligned with a second central longitudinal axis of the inner prong, wherein the inner post includes a first side wall and a second side wall, wherein the first outer post and the second outer post are spaced laterally away from one another along the outer prong such that the first outer post is positioned laterally outward from the first side wall of the inner post and the second outer post is positioned laterally outward from the second side wall of the inner post. The inner post can be configured to apply pressure to an inner portion of the nose of the patient, and wherein the first outer post can be configured to apply pressure to a first outer portion of the nose of the patient that is spaced laterally outwardly from the inner portion of the patient's nose, and wherein the second outer post is configured to apply pressure to a second outer portion of the nose of the patient that is spaced laterally outwardly from the inner portion of the patient's nose. The inner post can be configured to apply pressure to a portion of the nose of the patient and the portion of the nose of the patient can be configured to be positioned between the first outer post and the second outer post when the inner prong and the outer prong are secured to the patient. The detector can be coupled to the inner post. The outer prong can include a third outer post comprising a flexible flap coupled to the emitter. The first and second outer posts of the outer prong can be curved to conform to a portion of the nose of the patient. The inner prong can be curved to conform to a portion of the nose of the patient. The first outer post can have a first radius of curvature and a first curve direction, and the second outer post can have a second radius of curvature and a second curve direction, the first radius of curvature being equal to the second radius of curvature and the first curve direction being the same as the second curve direction. The inner prong can be curved along a third radius of curvature and in a third direction, the third radius of curvature being equal to the first and second radius of curvature. The outer prong can be U-shaped. The inner prong can include an inner base, and the outer prong can include an outer base. The inner prong can include an intermediate region and the outer prong can include an intermediate region. The intermediate region of the inner prong can be curved such that the intermediate region extends towards the intermediate region of the outer prong. The monitoring device can include a coupling portion configured to space the inner prong from the outer prong, wherein the coupling portion provides support to the inner and outer prongs to secure the device to the nose of the patient. The inner prong can include an inner base, and the outer prong can include an outer base. The inner post can be wider than the first outer post and the second outer post. The coupling portion can include the inner base and the outer base and the inner base can include a top surface and the outer base can include a top surface. The inner post can extend from a center of the top surface of the inner base. The first outer post can be spaced apart from the second outer post on the top surface of the outer base, and the first outer post and the second outer post can extend from the top surface of the outer base. The monitoring device can include a joint configured to rotatably connect the inner prong and the outer prong, the joint including a first joint portion coupled to the inner prong and a second joint portion coupled to the outer prong, wherein the first joint portion has a first slot and the second joint portion has a second slot, the first slot and the second slot configured to at least partially receive a pin. The monitoring device can include a biasing member configured to bias the inner prong from the outer prong. The biasing member can comprise a spring. The spring can be cylindrical or non-cylindrical. At least one of the outer prong or the inner prong can comprise a recess configured to secure at least a portion of the spring. At least one of the outer prong or the inner prong can comprise two protruding rims configured to secure at least a portion of the spring. The two protruding rims can be configured to secure to at least a portion of the spring by a snap-fit, press-fit, and/or friction-fit. The spring can include coils, a first leg, and a second leg. The first leg of the spring can extend in the same direction, or alternatively, an opposite direction as the second leg. The first leg of the spring can be parallel, non-parallel, or perpendicular to the second leg. The coupling portion can comprise a joint configured to rotatably connect the inner prong and the outer prong, the joint including a first joint portion coupled to the inner prong and a second joint portion coupled to the outer prong, wherein the first joint portion has a first slot and the second joint portion has a second slot, the first slot and the second slot configured to at least partially receive a pin.

A method of calculating a measurement of physiological parameters of a patient can comprise: transmitting light, by an emitter of a nose sensor, of at least first and second wavelengths through tissue of a nose of a patient to a detector; detecting, by the detector of the nose sensor, light attenuated by the tissue of the nose of the patient; generating an output signal, by the nose sensor, based on the light detected at the nose of the patient; and determining the measurement of the physiological parameters, by the nose sensor, based on the output signal. The method can include adhering the emitter with an adhesive to an outer surface of the nose of the patient. The method can include removing a liner from the emitter before adhering the emitter to the outer surface of the nose of the patient. The method can include focusing light into the detector with a lens. The lens can comprise glass, plastic, or both glass and plastic. The lens can comprise a simple lens. The lens can comprise one layer of material selected from the group consisting of glass and plastic. The lens can comprise at least two layers. The at least two layers can comprise a material selected from the group consisting of glass and plastic. The lens can comprise two or more simple lenses arranged about a common axis. The method can include diffusing light emitted by the emitter prior to entering the tissue of the nose of the patient with a diffuser. The diffuse can be located proximate to the emitter. The diffuser can comprise silicone. The diffuser can comprise white silicone, black silicone, acrylic, glass, and/or plastic. The diffuser can comprise two or more layers. Each of the two or more layers of the diffuser can comprise the same or different materials. The method can include transmitting the measurement of physiological parameters by the nose sensor based on the output signal with a transmitter. The transmitter can comprise a cable and/or a wireless transmitter. The wireless transmitter can be configured to operate on a protocol selected from the group consisting of Wi-Fi, Bluetooth, ZigBee, Z-wave, radio frequency, cellular telephony, infrared, and satellite transmission. The nose sensor can include: an inner prong configured to be positioned on one of an inner or outer side of a nose; and an outer prong configured to be positioned on one of an inner or outer side of a nose, wherein the detector is coupled to one of the inner or outer prongs and configured to be secured to a wall of the nose of the patient. The inner prong can be parallel, non-parallel, or perpendicular to the outer prong. The emitter can be coupled to a first end of a flexible circuit and the detector can be coupled to a second end of the flexible circuit, wherein a first portion of the flexible circuit is contained within the noninvasive physiological monitoring device and a second portion of the flexible circuit is not contained within the noninvasive physiological monitoring device, and the second portion is closer to the first end of the flexible circuit than to the second end, wherein the method further comprises securing the emitter to the nose of the patient. The inner prong can include an inner post and the outer prong can include a first outer post and a second outer post. The nose sensor of the method can include a first central longitudinal axis of the inner post aligned with a second central longitudinal axis of the inner prong, wherein the first outer post of the outer prong is spaced from the second outer post of the outer prong such that the first outer post has a first side wall that is positioned adjacent a second side wall of the outer prong and the second outer post has a third side wall that is positioned adjacent to a fourth side wall of the outer prong that is positioned opposite the second side wall of the outer prong. The nose sensor of the method can include a first central longitudinal axis of the inner post aligned with a second central longitudinal axis of the inner prong, wherein the inner post includes a first side wall and a second side wall, wherein the first outer post and the second outer post are spaced laterally away from one another along the outer prong such that the first outer post is positioned laterally outward from the first side wall of the inner post and the second outer post is positioned laterally outward from the second side wall of the inner post. The inner post can be configured to apply pressure to an inner portion of the nose of the patient, wherein the first outer post is configured to apply pressure to a first outer portion of the nose of the patient that is spaced laterally outwardly from the inner portion of the patient's nose, and wherein the second outer post is configured to apply pressure to a second outer portion of the nose of the patient that is spaced laterally outwardly from the inner portion of the patient's nose. The inner post can be configured to apply pressure to a portion of the nose of the patient and wherein the portion of the nose of the patient is configured to be positioned between the first outer post and the second outer post when the inner prong and the outer prong are secured to the patient. The outer prong can include a third outer post comprising a flexible flap coupled to the emitter. The first and second outer posts of the outer prong can be curved to conform to a portion of the nose of the patient. The inner prong can be curved to conform to a portion of the nose of the patient. The first outer post can have a first radius of curvature and a first curve direction, and the second outer post can have a second radius of curvature and a second curve direction, the first radius of curvature being equal to the second radius of curvature and the first curve direction being the same as the second curve direction. The inner prong can be curved along a third radius of curvature and in a third direction, the third radius of curvature being equal to the first and second radius of curvatures and the third direction being the same as the first and second curve directions. The outer prong can be U-shaped. The inner prong can include an inner base, and the outer prong can include an outer base. The inner prong can include an intermediate region and the outer prong can include an intermediate region. The intermediate region of the inner prong can be curved such that the intermediate region of the inner prong extends towards the intermediate region of the outer prong. The nose sensor of the method can include a coupling portion configured to space the inner prong from the outer prong, wherein the coupling portion provides support to the inner and outer prongs to secure the device to the nose of the patient. The inner prong can include an inner base, and the outer prong can include an outer base. The coupling portion can include the inner base and the outer base, wherein the inner base includes a first top surface and the outer base includes a second top surface. The inner post can extend from a center of the first top surface of the inner base. The first outer post can be spaced apart from the second outer post, and the first outer post and the second outer post can extend from the second top surface of the outer base. The inner post can be wider than the first outer post and the second outer post. The nose sensor of the method can include a joint configured to rotatably connect the inner prong and the outer prong, the joint including a first joint portion coupled to the inner prong and a second joint portion coupled to the outer prong, wherein the first joint portion has a first slot and the second joint portion has a second slot, the first slot and the second slot configured to at least partially receive a pin. The method can include biasing the inner prong from the outer prong with a biasing member. The biasing member can comprise a spring. The spring can be cylindrical or non-cylindrical. At least one of the outer prong or the inner prong can comprise a recess configured to secure at least a portion of the spring. At least one of the outer prong or the inner prong can comprise two protruding rims configured to secure at least a portion of the spring. The two protruding rims can be configured to secure at least a portion of the spring by a snap-fit, press-fit, and/or a friction-fit. The spring can comprise coils, a first leg, and a second leg. The first leg can extend in the same, or opposite, direction as the second leg. The first leg can be parallel, non-parallel, or perpendicular to the second leg. The first leg of the spring can extend in the same direction as the second leg. The coupling portion can comprise a joint configured to rotatably connect the inner prong and the outer prong, the joint including a first joint portion coupled to the inner prong and a second joint portion coupled to the outer prong, wherein the first joint portion has a first slot and the second joint portion has a second slot, the first slot and the second slot configured to at least partially receive a pin.

BRIEF DESCRIPTION OF THE DRAWINGS

Various examples will be described hereinafter with reference to the accompanying drawings. These examples are illustrated and described by example only, and are not intended to limit the scope of the disclosure. In the drawings, similar elements have similar reference numerals.

DETAILED DESCRIPTION

The present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, the systems, devices, and/or methods disclosed herein can include several novel features, no single one of which is solely responsible for its desirable attributes or which is essential to practicing the systems, devices, and/or methods disclosed herein.

General

This disclosure describes noninvasive sensor systems that can enable a user to measure, view, compare, analyze, evaluate, and/or download information relating to the respiratory system, for example, via a computing device, which may contain more advanced functionality than traditional systems and devices. The computing device can be, for instance, a cellphone or smartphone, tablet, laptop, personal digital assistant (PDA), and/or the like.

Generally, the embodiments described herein can involve, be integrated with, and/or depict several example user interfaces that may be implemented in a user computing device. The user interfaces shown, described, and/or discussed can depict example displays generated by the noninvasive sensor system and may be implemented in any of the user devices described herein.

The user interfaces shown, described, and/or discussed may be implemented in a mobile application such as an application that runs on a mobile operating system such as the Android™ operating system available from Google™ or the iOS™ operating system available from Apple™. Alternatively, or in addition to being a mobile application, the user interfaces shown, described, and/or discussed can be implemented in a web application that runs in a browser.

The user interfaces shown, described, and/or discussed are merely examples that illustrate some example embodiments described herein and may be varied in other embodiments. For instance, user interface controls shown may include buttons, touch-selective components and the like which may be altered to include any type of user interface control including, but not limited to, checkboxes, radio buttons, select boxes, dropdown boxes, textboxes or any combination of the same. Likewise, the different user interface controls may be combined or their functionality may be spread apart amongst additional controls while retaining the similar or same functionality as shown and described herein. Although touchscreen interfaces are shown, other devices may implement similar user interfaces with other types of user input devices such as a mouse, keyboard, stylus, or the like.

Figure 1:
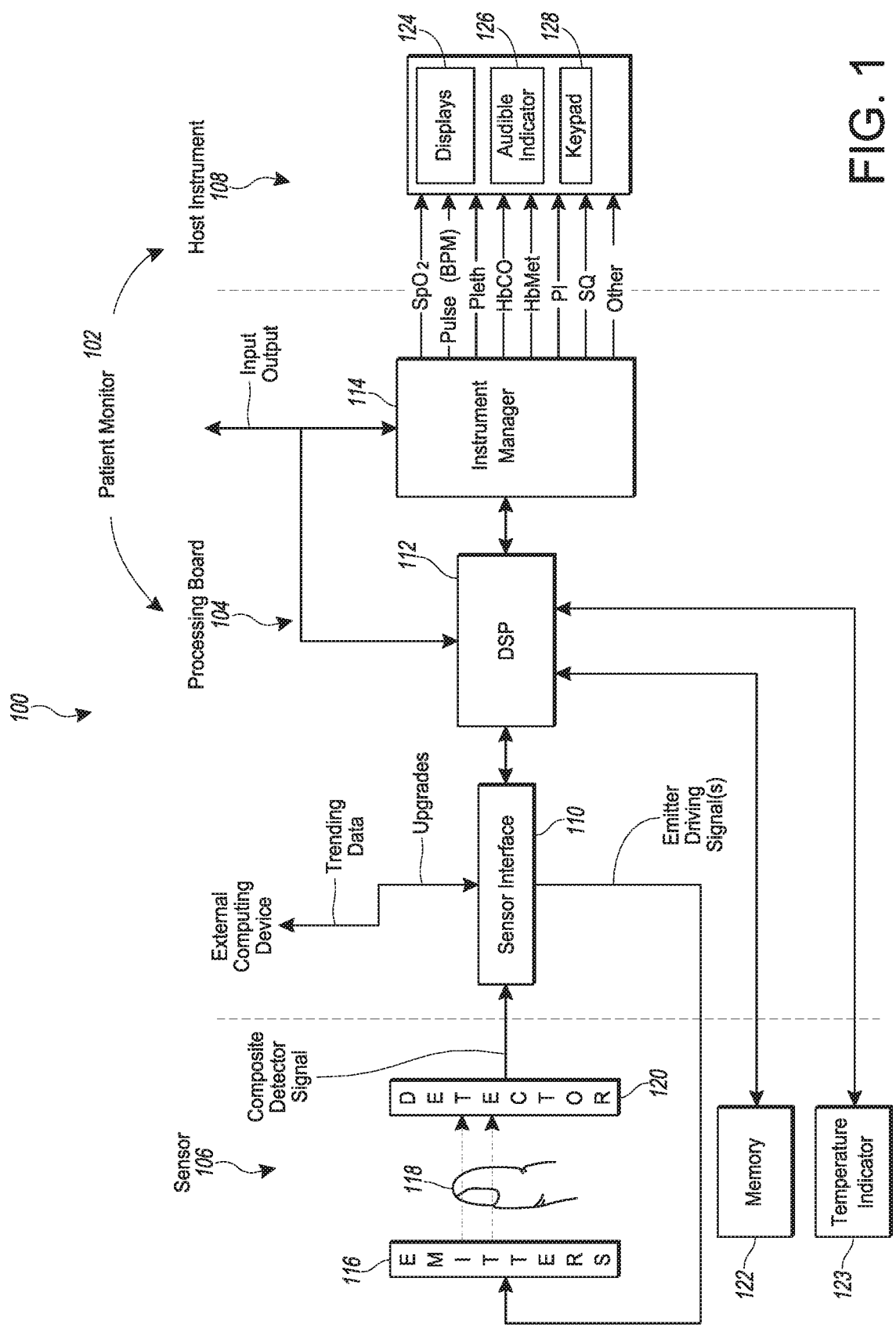
FIG. 1 illustrates a block diagram depicting a computer hardware system configured to run software for implementing one or more examples of the sensor system described herein.

FIG. 1 illustrates a block diagram of an exemplary user monitoring system 100. As shown in FIG. 1, the system 100 can include a user monitor 102 comprising a processing board 104 and a host instrument 108. The processing board 104 communicates with a sensor 106 to receive one or more intensity signal(s) indicative of one or more parameters of tissue of a user. The processing board 104 also communicates with a host instrument 108 to display determined values calculated using the one or more intensity signals. The processing board 104 can include processing circuitry arranged on one or more printed circuit boards capable of installation into the monitor 102, or capable of being distributed as some or all of one or more OEM components for a wide variety of host instruments monitoring a wide variety of user information. The processing board 104 can include a sensor interface 110, a digital signal processor and signal extractor ("DSP" or "processor") 112, and an instrument manager 114. In general, the sensor interface 110 can convert digital control signals into analog drive signals capable of driving sensor emitters, and converts composite analog intensity signal(s) from light sensitive detectors into digital data.

The sensor interface 110 can manage communication with external computing devices. For example, a multipurpose sensor port (or input/output port) can connect to the sensor 106 or alternatively connect to a computing device, such as a personal computer, a PDA, additional monitoring equipment or networks, or the like. When connected to the computing device, the processing board 104 may upload various stored data for, for example, off-line analysis and diagnosis. The stored data may comprise trend data for any one or more of the measured parameter data, plethysmograph waveform data acoustic sound waveform, or the like. Moreover, the processing board 104 may advantageously download from the computing device various upgrades or executable programs, may perform diagnosis on the hardware or software of the monitor 102. In addition, the processing board 104 may advantageously be used to view and examine user data, including raw data, at or away from a monitoring site, through data uploads/downloads, or network connections, combinations, or the like, such as for customer support purposes including software maintenance, customer technical support, and the like. Upgradable sensor ports are disclosed in U.S. Pat. No. 7,500,950, filed on Jul. 23, 2004, titled "Multipurpose Sensor Port," incorporated by reference herein.

As shown in FIG. 1, the digital data is output to the DSP 112. The DSP 112 can comprise a processing device based on the Super Harvard ARChitecture ("SHARC"), such as those commercially available from Analog Devices. However, a skilled artisan will recognize from the disclosure herein that the DSP 112 can comprise a wide variety of data and/or signal processors capable of executing programs for determining physiological parameters from input data. In particular, the DSP 112 includes program instructions capable of receiving multiple channels of data related to one or more intensity signals representative of the absorption (from transmissive or reflective sensor systems) of a plurality of wavelengths of emitted light by body tissue. The DSP 112 can accept data related to the absorption of eight (8) wavelengths of light, although an artisan will recognize from the disclosure herein that the data can be related to the absorption of two (2) to sixteen (16) or more wavelengths.

FIG. 1 also shows the processing board 104 including the instrument manager 114. The instrument manager 114 can comprise one or more microcontrollers controlling system management, including, for example, communications of calculated parameter data and the like to the host instrument 108. The instrument manager 114 may also act as a watchdog circuit by, for example, monitoring the activity of the DSP 112 and resetting it when appropriate.

The sensor 106 can comprise a reusable clip-type sensor, a disposable adhesive-type sensor, a combination sensor having reusable and disposable components, or the like. Moreover, an artisan will recognize from the disclosure herein that the sensor 106 can also comprise mechanical structures, adhesive or other tape structures, Velcro wraps or combination structures specialized for the type of user, type of monitoring, type of monitor, or the like. The sensor 106 can provide data to the board 104 and vice versa through, for example, a user cable. An artisan will also recognize from the disclosure herein that such communication can be wireless, over public or private networks or computing systems or devices, or the like. For example, such communication can be via wireless protocols such as Wi-Fi, Bluetooth, ZigBee, Z-wave, or radio frequency such as near field communication, or other wireless protocols such as cellular telephony infrared, satellite transmission, proprietary protocols, combinations of the same, and the like.

As shown in FIG. 1, the sensor 106 includes a plurality of emitters 116 irradiating the body tissue 118 with differing wavelengths of light, and one or more detectors 120 capable of detecting the light after attenuation by the tissue 118. The emitters 116 can include a matrix of eight (8) emission devices mounted on a flexible substrate, the emission devices being capable of emitting eight (8) differing wavelengths of light. The emitters 116 can comprise twelve (12) or sixteen (16) emitters, although other numbers of emitters are contemplated, including two (2) or more, three (3) or more, four (4) or more, five (5) or more, six (6) or more, or seven (7) or more emitters, for example. As shown in FIG. 1, the sensor 106 may include other electrical components such as, for example, a memory device 122 comprising an EPROM, EEPROM, ROM, RAM, microcontroller, combinations of the same, or the like. Other sensor components may include an optional temperature determination device 123 or other mechanisms for, for example, determining real-time emission wavelengths of the emitters 116.

The memory 122 may advantageously store some or all of a wide variety data and information, including, for example, information on the type or operation of the sensor 106; type or identification of sensor buyer or distributor or groups of buyer or distributors, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters for which the sensor is capable of supplying sufficient measurement data (e.g., HbCO, HbMet, HbT, or the like), calibration or parameter coefficient data, software such as scripts, executable code, or the like, sensor electronic elements, whether the sensor is a disposable, reusable, multi-site, partially reusable, partially disposable sensor, whether it is an adhesive or non-adhesive sensor, whether the sensor is a reflectance, transmittance, or transreflectance sensor, whether the sensor is a finger, hand, foot, forehead, or ear sensor, whether the sensor is a stereo sensor or a two-headed sensor, sensor life data indicating whether some or all sensor components have expired and should be replaced, encryption information, keys, indexes to keys or hash functions, or the like, monitor or algorithm upgrade instructions or data, some or all of parameter equations, information about the user, age, sex, medications, and other information that may be useful for the accuracy or alarm settings and sensitivities, trend history, alarm history, or the like. The monitor may advantageously store data on the memory device, including, for example, measured trending data for any number of parameters for any number of users, or the like, sensor use or expiration calculations, sensor history, or the like.

FIG. 1 also shows the user monitor 102 including the host instrument 108. The host instrument 108 can communicate with the board 104 to receive signals indicative of the physiological parameter information calculated by the DSP 112. The host instrument 108 preferably includes one or more display devices 124 capable of displaying indicia representative of the calculated physiological parameters of the tissue 118 at the measurement site. The host instrument 108 can advantageously include a handheld housing capable of displaying one or more of a pulse rate, plethysmograph data, perfusion quality such as a perfusion quality index ("PI™"), signal or measurement quality ("SQ"), values of blood constituents in body tissue, including, for example, $SpO_2$, HbCO, HbMet, HbT, or the like. The host instrument 108 can display values for one or more of HbT, Hb, blood glucose, bilirubin, or the like. The host instrument 108 may be capable of storing or displaying historical or trending data related to one or more of the measured values, combinations of the measured values, plethysmograph data, or the like.

The host instrument 108 also includes an audio indicator 126 and user input device 128, such as, for example, a keypad, touch screen, pointing device, voice recognition device, or the like.

The host instrument 108 can include audio or visual alarms that alert caregivers that one or more physiological parameters are falling below predetermined safe thresholds. The host instrument 108 can include indications of the confidence a caregiver should have in the displayed data. The host instrument 108 can advantageously include circuitry capable of determining the expiration or overuse of components of the sensor 106, including, for example, reusable elements, disposable elements, or combinations of the same.

Although described in terms of certain systems, other systems or combination of systems will be apparent to those of ordinary skill in the art from the disclosure herein. For example, the monitor 102 may comprise one or more monitoring systems monitoring parameters, such as, for example, vital signs, blood pressure, ECG or EKG, respiration, glucose, bilirubin, or the like. Such systems may combine other information with intensity-derived information to influence diagnosis or device operation. Moreover, the monitor 102 may advantageously include an audio system, preferably comprising a high quality audio processor and high quality speakers to provide for voiced alarms, messaging, or the like. The monitor 102 can advantageously include an audio out jack, conventional audio jacks, headphone jacks, or the like, such that any of the display information disclosed herein may be audibilized for a listener. For example, the monitor 102 may include an audible transducer input (such as a microphone, piezoelectric sensor, or the like) for collecting one or more of heart sounds, lung sounds, trachea sounds, or other body sounds and such sounds may be reproduced through the audio system and output from the monitor 102. Also, wired or wireless communications (such as Bluetooth® or WiFi, including IEEE 801.11a, b, or g), mobile communications, combinations of the same, or the like, may be used to transmit the audio output to other audio transducers separate from the monitor 102. Other communication protocols can also be utilized. For example, such communication can be via wireless protocols such as ZigBee, Z-wave, or radio frequency such as near field communication, or other wireless protocols such as cellular telephony infrared, satellite transmission, proprietary protocols, combinations of the same, and the like.

Patterns or changes in the continuous noninvasive monitoring of intensity-derived information may cause the activation of other vital sign measurement devices, such as, for example, blood pressure cuffs.

Sensor System

This disclosure describes patient monitoring devices that can include one or more sensors that can be worn by a patient. For example, the patient monitoring devices discussed in this disclosure can include one or more, two or more, three or more, four or more, or five or more sensors that can be worn by a patient. The systems described herein and shown in the attached drawings include sensors and sensor systems for measuring physiological parameters. Sensors and physiological monitors described herein include hardware and/or software capable of determining, comparing, analyzing, and/or monitoring blood oxygenation levels in veins, arteries, a heart rate, a blood flow, respiratory rates, and/or other physiological parameters. For example, a pulse oximetry system can use an optical sensor clipped onto a patient's nose, to measure a relative volume of oxygenated hemoglobin in pulsatile arterial blood flowing within, the fingertip, foot, ear, forehead, or other measurement sites.

The patient monitoring device discussed herein can be shaped and sized for use in various environmental settings and/or for use in various applications. For example, as described above, using the nose sensor, a medical patient can be monitored using one or more sensors, each of which can transmit a signal over a cable or other communication link or medium such as those discussed herein to a physiological monitor. A nose sensor can be placed on the alar region of the nose. As referred to herein, "nose" can include any portion of a patient's nose. For example, the patient's nose can include at least a portion of the patient's nostril, the alar region of the nose, an inner surface of the nose, and/or an outer surface of the nose, among other portions. As described above, the nose sensor can measure internal and/or external carotid arteries, veins, and/or other vessels to determine blood oxygenation levels and/or changes, heart rates, blood flow measurements, respiratory rates, and/or the like.

The nose sensor can also include sensing elements such as, for example, acoustic piezoelectric devices, electrical ECG leads, pulse oximetry sensors, and/or the like. The sensors can generate respective signals by measuring one or more physiological parameters of the patient. The sensors can generate respective signals by measuring one or more, two or more, three or more, four or more, five or more, six or more, seven or more, eight or more, or nine or more physiological parameters of the patient, for example. The signals can then be processed by one or more processors. The one or more processors then can communicate the processed signal to a display if a display is provided. The display can be incorporated in the physiological monitor. The display can be separate from the physiological monitor. The nose sensor can have one or more cables connecting the sensor to a monitor, other sensors, and/or a display, among other components. Alternatively, or additionally, the nose sensor can have a wireless transmitter, receiver, or transceiver for receiving and/or transmitting information regarding physiological parameters to a display or stand-alone monitor. The wireless transmitter, receiver, or transceiver of the nose sensor can utilize the communication links or protocols discussed herein. For example, such communication can be via wireless protocols such as Wi-Fi, Bluetooth, ZigBee, Z-wave, or radio frequency such as near field communication, or other wireless protocols such as cellular telephony infrared, satellite transmission, proprietary protocols, combinations of the same, and the like.

FIGS. 2-8 illustrate a nose sensor system 200. The nose sensor system 200 can include an inner prong 202 and an outer prong 204. The inner prong 202 can be coupled to the outer prong 204 by a coupling portion 220 (see FIGS. 4 and 6).

The coupling portion 220 can be formed at an intersection between the inner prong 202 and the outer prong 204. The coupling portion 220 can be positioned approximately at a center of the outer prong 204. For example, the inner prong 202 and the outer prong 204 can be coupled by the coupling portion 220. The coupling portion 220 can be generally rounded. The coupling portion 220 can be square, rectangular, and/or triangular. The coupling portion 220 can comprise a combination of these styles and/or shapes. The coupling portion 220 can help to maintain the rigidity of the sensor 200. The coupling portion 220 can bias the outer prong 204 towards the inner prong 202 and/or the inner prong 202 towards the outer prong 204. The coupling portion 220 can space the outer prong 204 from the inner prong 202 to accommodate various nose geometries.

The inner prong 202 and the outer prong 204 can be integrally formed. The inner prong 202, outer prong 204, and/or the coupling portion 220 can be integrally formed. The inner prong 202 and/or the outer prong 204 can be formed separately and/or can be connected by the coupling portion 220. For example, the outer prong 204 can be adhered, bonded, formed with, and/or otherwise connected to the inner prong 202. Additionally, the outer prong 204 and/or the inner prong 202 can be adhered, bonded, formed with, and/or otherwise connected to the coupling portion 220. The outer prong 204 and/or the inner prong 202 can connect to the coupling portion 220 by a snap-fit connection. For example, the outer prong 204 can snap into and thereby secure to the coupling portion 220, and/or the coupling portion 220 can snap into and thereby secure to the outer prong 204. The inner prong 202 can snap into and thereby secure to the coupling portion 220, and/or the coupling portion 220 can snap into and thereby secure to the inner prong 202.

Figure 4:
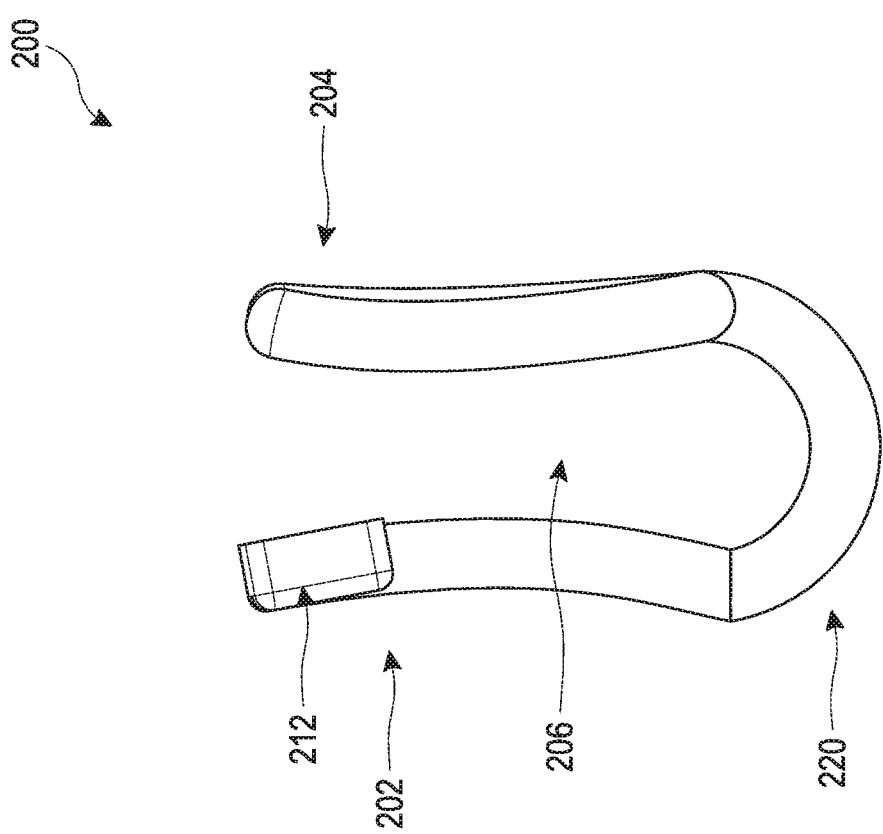
FIG. 4 illustrates a side view of the nose sensor of FIG. 2.

As shown, in FIG. 4, the inner prong 202 can extend away from the outer prong 204. The inner prong 202 can extend away from the coupling portion 220 in a first and/or second direction. The inner prong 202 can include a detector 212 as described in more detail below. At least a portion of the inner prong 202 can be configured to be positioned within a patient's nose. At least a portion of the inner prong 202 can be positioned adjacent an inner surface of a patient's nose. At least a portion of the inner prong 202 can engage at least a portion of an inner surface of a patient's nose. At least a portion of the inner prong 202 can be positioned within a patient's nose and/or at least a portion of the inner prong 202 can remain outside of the patient's nose when the nose sensor 200 is in use. Alternatively, at least a portion of the inner prong 202 can be configured to be positioned outside a patient's nose. At least a portion of the inner prong 202 can be positioned adjacent an outer surface of a patient's nose. At least a portion of the inner prong 202 can engage at least a portion of an outer surface of a patient's nose.

The inner prong 202 can include at least one inner post 203. The inner post 203 can be coupled with the detector 212 as discussed in more detail below. The inner post 203 can be configured to be positioned within the patient's nose.

Figure 2:
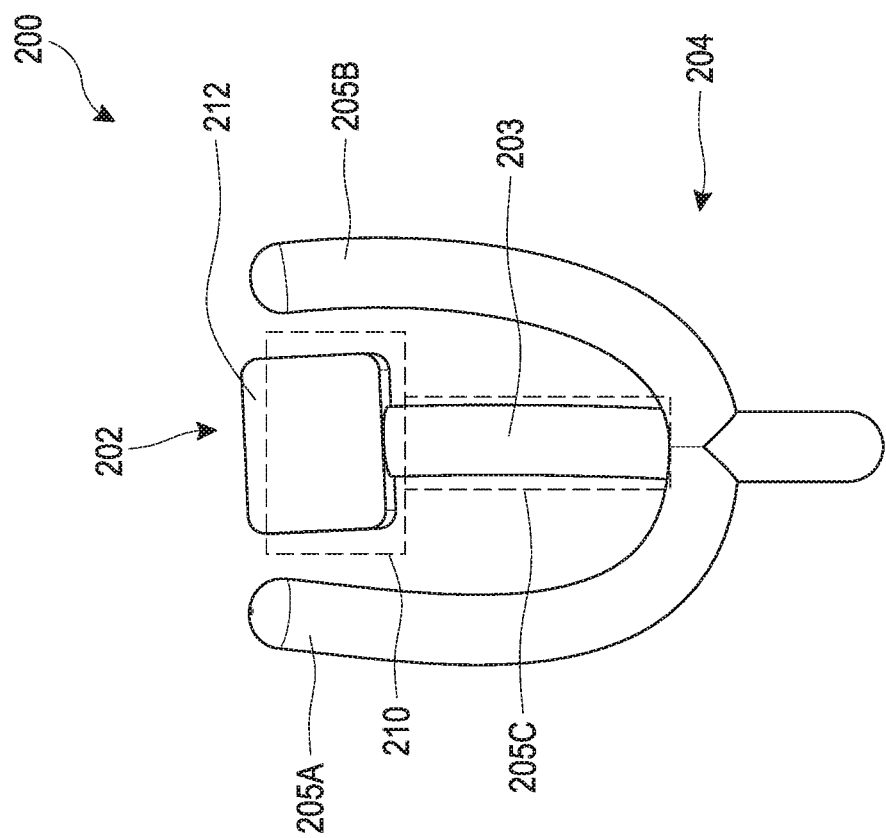
FIG. 2 illustrates a front view of a nose sensor.

As shown in FIG. 2, the outer prong 204 can be generally U-shaped. The outer prong 204 can comprise other shapes, however, such as a V-shape. The outer prong 204 can include at least one outer post 205. For example, the outer prong 204 can include one or more, two or more, three or more, or four or more outer posts 205. As shown in FIG. 2, the outer prong 204 can include two outer posts 205A, 205B. The outer posts 205A, 205B can be integrally formed. The outer posts 205A, 205B can be formed with the outer prong 204. The outer posts 205A, 205B can be connected directly to the coupling portion 220. The outer prong 204, the coupling portion 220, and/or the inner prong 202 can comprise various lengths. The outer prong 204 and/or the outer posts of the outer prong 204 can be longer than the inner prong 202, inner post 203, and/or the coupling portion 220. The outer prong 204 and/or the outer posts of the outer prong 204 can be shorter than the inner prong 202, inner post 203 and/or the coupling portion 220. Thus, the outer prong 204, coupling portion 220, the inner prong 202, and/or the inner post 203 can comprise various lengths so as to aid securement to patient's having varying sizes and/or shapes of noses. The outer prong 204, the coupling portion 220, the inner prong 202, and/or the inner post 203 can also comprise various lengths so as to aid comfort to patient's having varying sizes and/or shapes of noses when the nose sensor 200 or a portion thereof is attached to the patient.

As discussed above, the outer prong 204 can be generally U-shaped. The outer prong 204 can be rectangular-shaped, square-shaped, and/or triangle-shaped, among other shapes. The outer posts 205A, 205B can extend outwardly from the coupling portion 220. The outer posts 205A, 205B can be curved as the outer posts 205A, 205B extend away from the coupling portion 220. For example, a lower portion of the outer posts 205A, 205B can be generally curved. An upper portion of the outer posts 205A, 205B can extend generally upwardly from the lower portion. The upper portion of the outer posts 205A, 205B can extend inwardly towards one another and/or towards a coupling region 206 (see FIG. 4).

As shown in FIG. 4, for example, the outer prong 204 can be curved at an intermediate portion. The intermediate portion of the outer prong 204 and/or of the outer posts 205A, 205B can be curved towards the inner prong 202. The intermediate portion of the outer prong 204 and/or the outer posts 205A, 205B can be generally straight such that the outer prong 204 extends generally upwardly and/or parallel to the inner prong 202. The shape of the outer prong 204 can beneficially help to secure the nose sensor 200 to the patient's nose. For example, the shape of the outer prong 204 relative to the shape of the inner prong 202 can help to secure the nose sensor 200 to the patient's nose. As shown in FIG. 4, for example, an intermediate portion of the inner prong 202 and the outer prong 204 are curved towards one another to help to secure the nose sensor 200 to the patient's nose in use. This can advantageously help to minimize contact with the patient's nose to reduce the chance of irritating the patient's skin while also securing the nose sensor to the patient's nose. For example, only the intermediate region of the outer prong 204 and/or the inner prong 202 can contact the patient's tissue. At least a portion of a lower, intermediate, and/or upper portion of the outer prong 204 and/or at least a portion of a lower, intermediate, and/or lower portion of the inner prong 202 can contact the patient's tissue.

Figure 5:
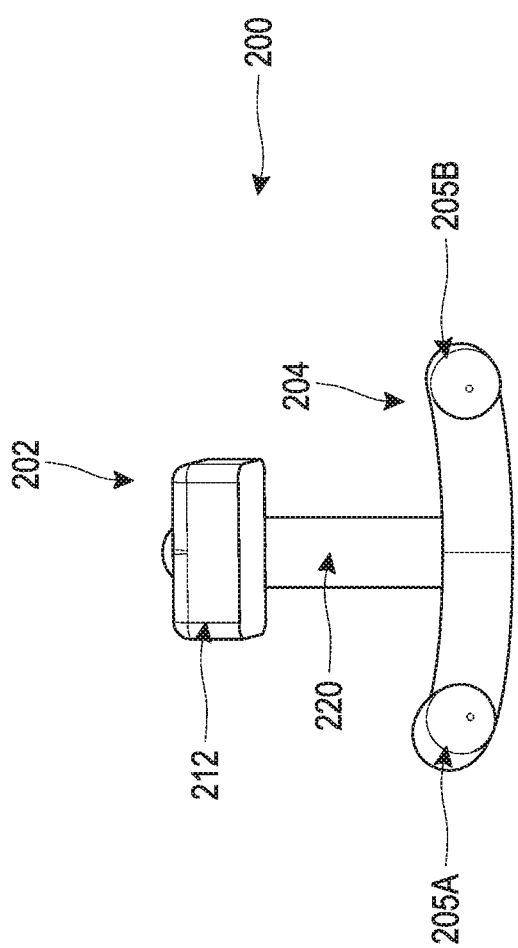
FIG. 5 illustrates a top view of the nose sensor of FIG. 2.
Figure 6:
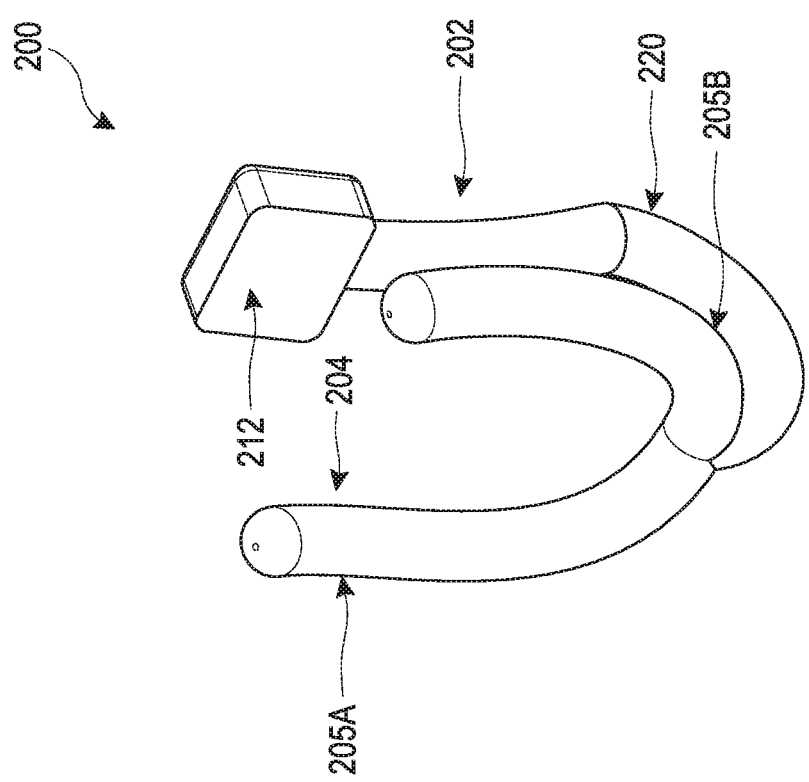
FIG. 6 illustrates a perspective view of the nose sensor of FIG. 2.

As shown in at least FIGS. 4 and 5, the outer prong 204 can be biased inwardly relative to the inner prong 202 and/or the inner prong 202 can be biased inwardly relative to the outer prong 204. For example, the inner prong 202 and/or the outer prong 204 can be biased such that the nose sensor 200 can be secured to the patient's nose between the inner prong 202 and the outer prong 204. This can enhance comfort to the patient when the nose sensor 200 is secured to the patient. The nose sensor 200 can be configured to accommodate various shaped and sized noses, and in particular, the alar of the nose. For example, to accommodate a larger nose, the outer prong 204 can be pulled away from the inner prong 202 and/or the inner prong 202 can be pulled away from the outer prong 204. In use, at least a portion of the nose sensor 200 can slide onto the patient's nose. When the nose sensor 200 slides along the patient's nose, the outer prong 204 and/or the inner prong 202 can bend and/or be pushed outwardly by the patient's tissue. This can help to ensure that the nose sensor 200 remains secured to the patient's nose and/or is comfortable to the patient. This can help to allow the nose sensor 200 to sit flush against the patient's tissue, inside, and/or outside of the patient's nose. The nose sensor 200 may be less bulky and/or occupy less space on the patient's tissue. For example, the reduced profile of the inner prong 202 can allow for a larger breathing space within the patient's nasal passages if the inner prong 202 is configured to be inserted into the patient's nose when nose sensor 200 is secured to the patient.

The outer prong 204, outer posts 205A and 205B, the inner post 203, the third post 205C (see FIGS. 7, 8), and/or the coupling portion 220 can comprise a cross-section that is circular. Alternatively, the outer prong 204, outer posts 205A and 205B, the inner post 203, the third post 205C, and/or the coupling portion 220 can comprise a cross-section that is non-circular. For example, the outer prong 204, outer posts 205A and 205B, the inner post 203, the third post 205C, and/or the coupling portion 220 can comprise a cross-section that is polygonal. The outer prong 204, outer posts 205A and 205B, the inner post 203, the third post 205C, and/or the coupling portion 220 can comprise a cross-section that is triangle, quadrilateral, pentagonal, hexagonal, heptagonal, octagonal, nonagonal, decagonal, or otherwise shaped. The outer prong 204, outer posts 205A and 205B, the inner post 203, the third post 205C, and/or the coupling portion 220 can comprise a cross-section that is some combination of these circular and/or polygonal shapes. For example, the outer prong 204, outer posts 205A and 205B, the inner post 203, the third post 205C, and/or the coupling portion 220 can comprise a cross-section that is partially circular and partially polygonal.

Figure 7:
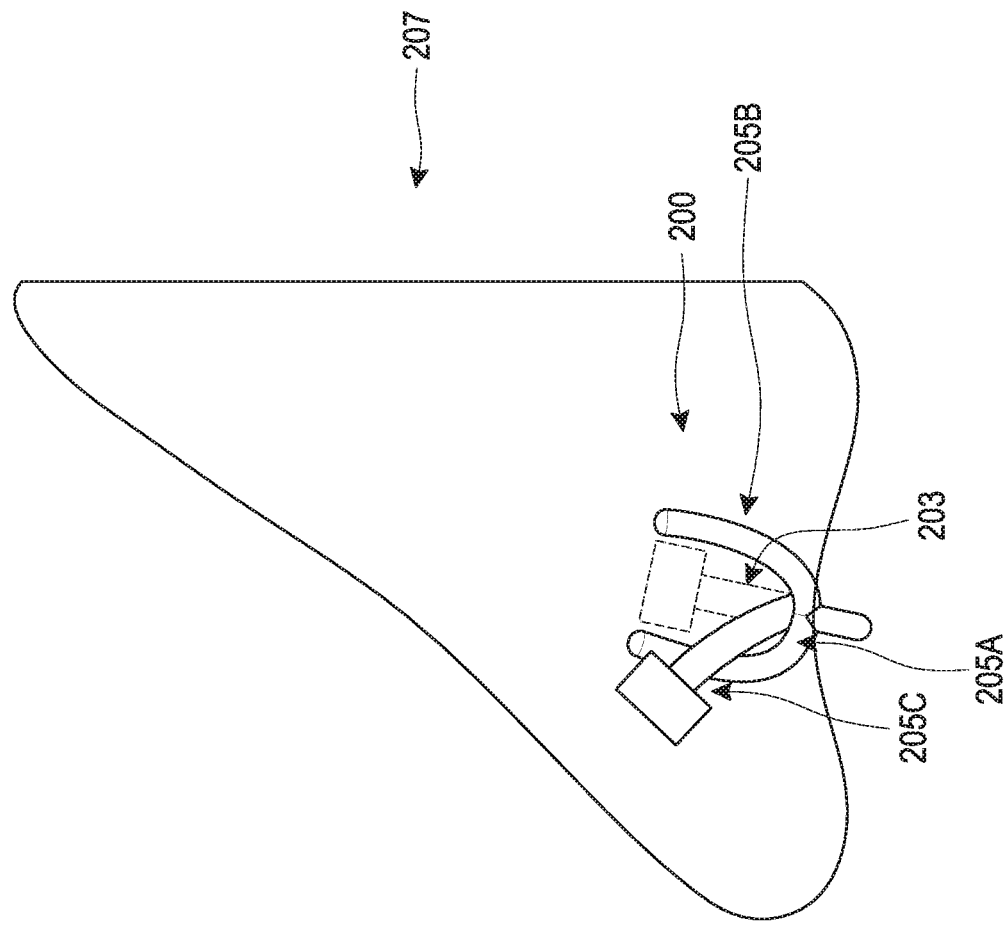
FIG. 7 illustrates a perspective view of the nose sensor of FIG. 2 in use.
Figure 8:
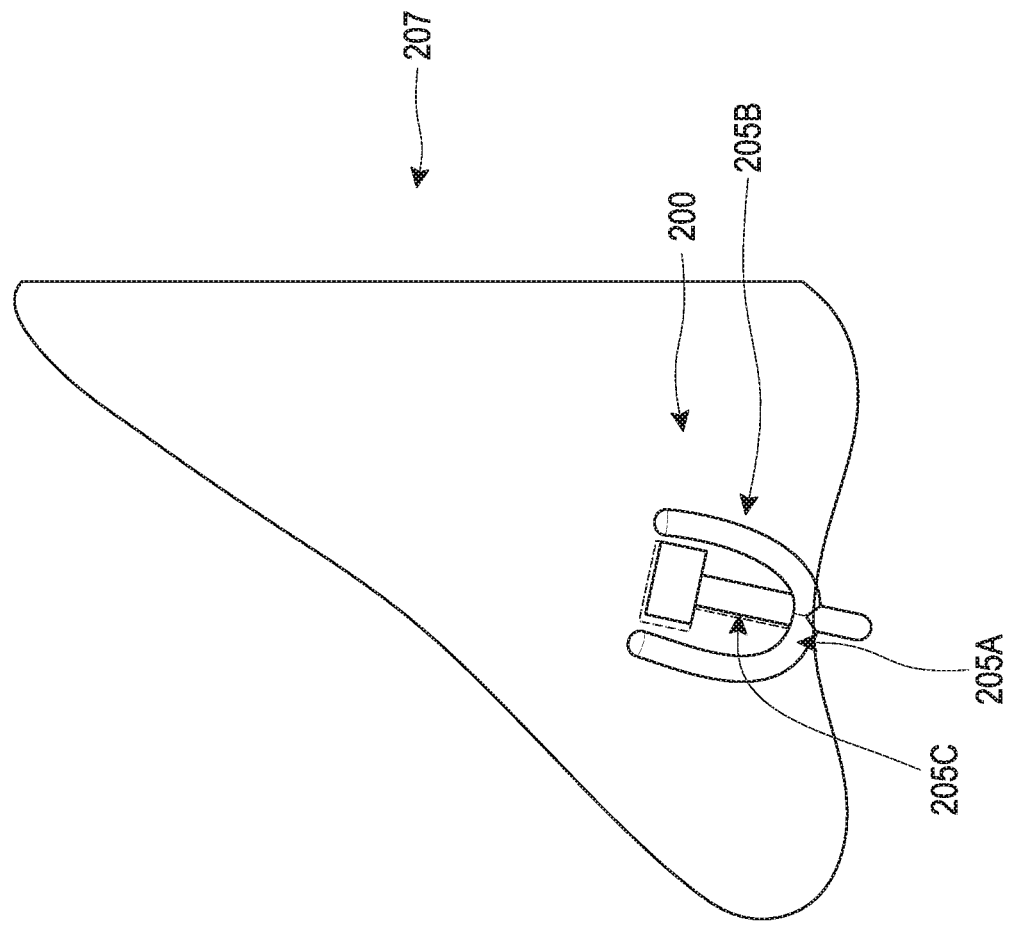
FIG. 8 illustrates a perspective view of the nose sensor of FIG. 2 in use.

FIGS. 7 and 8 illustrate the nose sensor 200 in use. As shown, at least a portion of the inner post 203 can slide into the patient's nose and engage an inner surface of the patient's nose. At least a portion of the outer posts 205A, 205B can slide along an outer region of the patient's nose and engage an outer surface of the patient's nose. Alternatively, at least a portion of the inner prong 202 and/or the inner post 203 can slide along an outer region of the patient's nose and engage an outer surface of the patient's nose, and at least a portion of the outer posts 205A, 205B can slide into the patient's nose and engage an inner surface of the patient's nose. These configurations can help to ensure that the nose sensor 200 remains secured to the patient's nose and/or is comfortable when secured to the patient. These configurations can help to allow the nose sensor 200 to sit flush against the patient's tissue, inside and/or outside of the patient's nose. The sensor 200 may be less bulky and/or occupy less space on the patient's tissue. For example, as shown in FIG. 2, a central longitudinal axis of the inner post 203 can be aligned with or parallel to a central longitudinal axis of the inner prong 202. The first outer post 205A can be spaced from the second outer post 205B. For example, the first outer post 205A can have a side wall that is positioned adjacent a first side wall of the outer prong 204 and the second outer post 205B can have a side wall that is positioned adjacent an second side wall of the outer prong 204.

Figure 3:
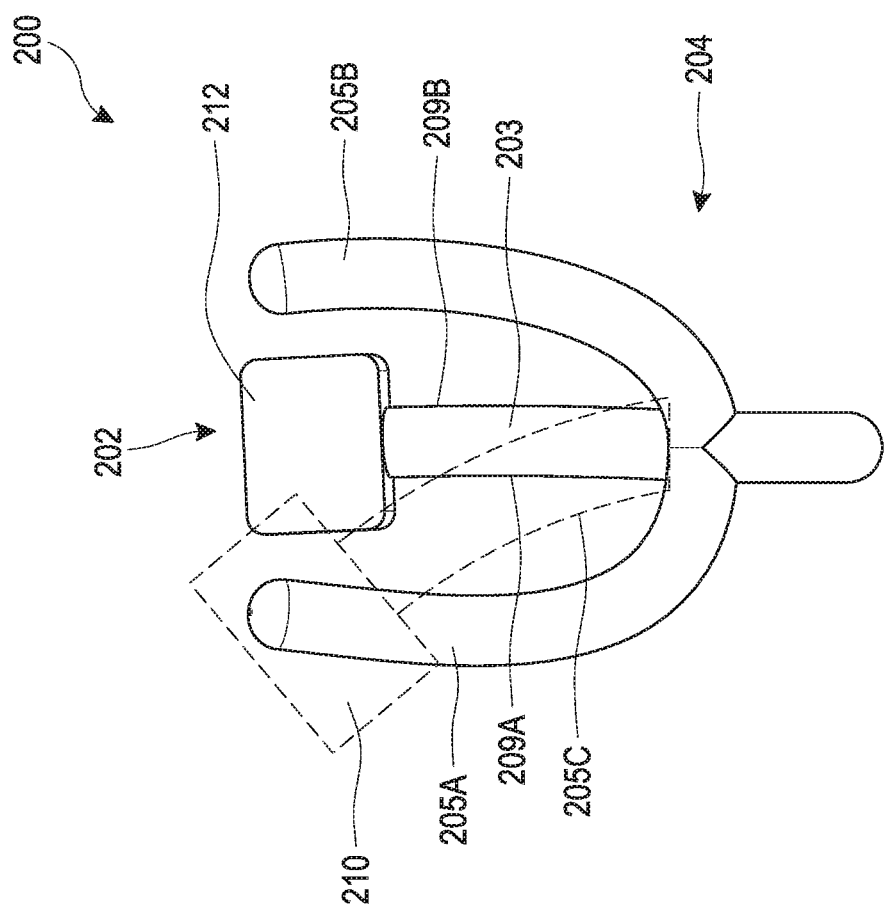
FIG. 3 illustrates a front view of the nose sensor of FIG. 2.

As shown in the illustrated nose sensor 200 in FIG. 3, the inner post 203 can include a first side wall 209A and a second side wall 209B. The first outer post 205A and/or the second outer post 205B can be spaced laterally away from one another along the outer prong 204. The first outer post 205A can be positioned laterally outward from the first side wall 209A of the inner post 203. The second outer post 205B can be positioned laterally outward from the second side wall 209B of the inner post 203.

The inner prong 202 (or a portion thereof) can apply pressure to an inner portion of the nose of the patient when the nose sensor 200 is secured to at least a portion of the patient's nose. The first outer post 205A can apply pressure to a portion of the nose of the patient that can be spaced laterally outwardly from at least a portion of the inner portion of the patient's nose where the inner prong 202 (or portion thereof) applies a pressure when the nose sensor 200 is secured to the patient. The second outer post 205B can apply pressure to a portion of the nose of the patient that can be spaced laterally outwardly from the inner portion of the patient's nose where the inner prong 202 (or portion thereof) applies a pressure when the nose sensor 200 is secured to the patient. The inner post 203 can apply pressure to a portion of the nose of the patient, as discussed above. The portion of the nose of the patient can be positioned between the first outer post 205A and/or the second outer post 205B when the inner prong 202 and the outer prong 204 of the nose sensor 200 are secured to the patient. The inner prong 202 (or portion thereof) can apply pressure to a portion of the nose of the patient. The portion of the nose of the patient can be positioned between the first outer post 205A and the second outer post 205B when the inner prong 202 and the outer prong 204 are secured to the patient.

To secure the nose sensor 200 to the patient, the inner prong 202 (or portion thereof) can apply pressure to an inner surface of the patient's nose, as discussed above. For example, the inner prong 202 (or portion thereof) can apply pressure from the inside of the patient's nose towards the outside of the patient's nose. The first outer post 205A and/or the second outer post 205B can apply pressure to the outer surface of the patient's nose. For example, the first and/or second outer posts 205A, 205B can apply pressure from the outside of the patient's nose towards the inside of the patient's nose. The inner prong 202 (or portion thereof) can apply pressure to a portion of the patient's nose that is positioned at least partially between the outer posts 205A, 205B. The outer posts 205A, 205B can apply pressure to a portion of the patient's nose that is positioned at least partially outwardly from the inner prong 202 (or portion thereof).

As discussed above, the positioning of the inner prong 202 and/or the outer prong 204 of the nose sensor 200 can advantageously help to secure the nose sensor 200 to the patient while also minimizing the contact of portions of the nose sensor 200 with the patient. As also discussed above, varying the positioning of portions of the nose sensor 200 and/or minimizing the contact between portions of the nose sensor 200 and the patient can aid patient comfort and improve securement. For example, the inner prong 202 (or portions thereof), the outer prong 204, and/or the coupling portion 220 can secure to the patient by contacting one or more points, areas, or portions of the patient's nose. For example, the inner prong 202 can contact an inner or outer portion of the patient's nose and the first and second outer posts 205A, 205B of the outer prong 204 can contact a different inner or outer portion of the patient's nose when the nose sensor 200 is secured to the patient. Compared to other sensors which may contact a larger portion or region of a patient's nose when secured to the patient, the configuration of the inner prong 202 and/or outer prong 204 of the nose sensor 200 can contact less of a portion or region of a patient's nose when the nose sensor 200 is secured to a patient. As discussed above, the inner prong 202 and/or outer prong 204 of the nose sensor 200 can be configured to contact a minimal amount of a portion or region of a patient's nose when the nose sensor 200 is secured to a patient.

The nose sensor 200 can measure various physiological parameters of a patient, as discussed above. As shown in FIGS. 2-8, for example, the nose sensor 200 can include an emitter 210 and a detector 212 to allow the nose sensor 200 to measure the patient's physiological parameters, such as those discussed herein.

Various arrangements of the emitter 210 and/or the detector 212 can allow the nose sensor 200 to take more accurate measurements. The emitter can be a light-emitting diode (LED). The emitter 210 can emit light of a certain wavelength. The light emitter 210 can emit light of different wavelengths in sequence with only one emitter emitting light at a given time, thereby forming a pulse sequence. The number of emitters is not limiting and can range from two to eight, or more in some instances. Detailed descriptions and additional examples of the light emitters are provided in U.S. Pat. No. 9,277,880, referenced above.

The detector 212 can detect light from the emitter 210 after the light passes through and is attenuated by tissue of the patient's nose. For example, the detector 212 can comprise photodetectors, photodiodes, phototransistors, and/or the like. Additional details of the photodetector are described in U.S. Pat. No. 9,277,880, referenced above. The detector 212 can generate an electrical signal based on the detected light from the emitter 210. The signal of the detected light from the emitter 210 can be input into a signal processor described herein, such that the signal processor can process an output of the sensor 200.

FIGS. 2-8 illustrate a detector 212. The detector 212 can be positioned along the inner prong 202. For example, the detector 212 can be coupled with an end of the inner post 203 of the inner prong 202. The detector 212 can be coupled with an upper edge of the inner post 203. The detector 212 can be coupled with an inner surface of the inner post 203. The detector 212 can be adhered, bonded, formed into, and/or otherwise attached to the inner post 203. The detector 212 can be configured to connect to the inner post 203 by a snap-fit connection. The inner post 203 and the detector 212 can be integrally formed. The detector 212 can be secured to an inner surface of the patient's tissue within the patient's nose.

The detector 212 can be secured to the inner surface of the patient's nose by an adhesive. Alternatively, the detector 212 can be secured to the inner surface of the patient's nose without adhesives. For example, the engagement of the outer prong 204 and/or the inner prong 202 with the patient's nose can hold the detector 212 against the inner surface of the patient's nose without the use of adhesives.

The detector 212 can be secured to the outer surface of the patient's nose by an adhesive. Alternatively, the detector 212 can be secured to the outer surface of the patient's nose without adhesives. For example, the engagement of the outer prong 204 and/or the inner prong 202 with the patient's nose can hold the detector 212 against the outer surface of the patient's nose without the use of adhesives.

The emitter 210 can be secured to the inner surface of the patient's nose by an adhesive. Alternatively, the emitter 210 can be secured to the inner surface of the patient's nose without adhesives. For example, the engagement of the outer prong 204 and/or the inner prong 202 with the patient's nose can hold the emitter 210 against the inner surface of the patient's nose without the use of adhesives.

The emitter 210 can be secured to the outer surface of the patient's nose by an adhesive. Alternatively, the emitter 210 can be secured to the outer surface of the patient's nose without adhesives. For example, the engagement of the outer prong 204 and/or the inner prong 202 with the patient's nose can hold the emitter 210 against the outer surface of the patient's nose without the use of adhesives. The emitter 210 and/or the detector 212 can include an adhesive layer and a release liner overtop the adhesive layer. The release liner can be removed when the emitter 210 and/or the detector 212 is ready to be secured to a patient's skins surface, such as an interior or exterior portion of a patient's nose.

The securement of the nose sensor 200 to the patient can be configured to maintain an alignment between the emitter 210 and detector 212 when the nose sensor 200 is in use, as discussed below. As shown in FIG. 4, the detector 212 can be angled away from the outer prong 204, the outer posts 205A, 205B, 205C and/or the emitter 210. The nose sensor 200 shape and/or size can be varied so as to reduce the bulkiness and/or the obtrusiveness of the nose sensor 200. Thus, the nose sensor 200 can maintain a generally low profile. The nose sensor 200 can include a diffuser positioned proximate to the emitter 210. For example, the diffuser can be positioned in front of the emitter 210. The diffuser can comprise silicone. For example, the diffuser can include white and/or black silicone or a combination thereof to scatter a greater amount of light and/or more accurately measure a patient's physiological parameters. For example, an inner part of the diffuser can be white or of a more translucent material and the outer part can be black or of a less translucent material in order to prevent scattering of light beyond the area of interest and to prevent stray ambient light from entering the tissue site. The diffuser can comprise materials other than silicone. For example, the diffuser can comprise acrylic and/or plastics such as polycarbonate and/or polycarbonate film or sheets. The diffuser can comprise glass such as opal glass, ground glass, patterned glass, and/or a combination of such materials. The diffuser can also comprise other materials with varying material properties and/or characteristics. The diffuser can comprise one or more layers with different material properties and/or characteristics. For example, the diffuser can comprise, two or more, three or more, four or more, five or more, six or more, seven or more, or eight or more layers with different material properties and/or characteristics. Additionally, the diffuser can comprise one or more layers with similar material properties and/or characteristics. For example, the diffuser can comprise, two or more, three or more, four or more, five or more, six or more, seven or more, or eight or more layers with similar material properties and/or characteristics.

The diffuser of the nose sensor 200 can diffuse emitted light prior to entering the tissue. The diffuser can advantageously spread out, disseminate, and/or scatter light exiting from the emitter 210 into and/or around a portion of a patient's body, for example the nose. This can permit light originating from the emitter 210 to pass through a wider region or area of a patient's body, and thus better facilitate collection of physiological parameters (such as those discussed above). The detector 212 can be sized and shaped to receive the optical radiation after it attenuates through tissue and fluids of a portion of a body. Diffusing light prior to entering the tissue can be advantageous because the light is allowed to pass through more tissue. This allows the light to sample more of the body tissue before being detected. It also provides for more even and consistent light across a larger portion of tissue. The diffusion of light by the diffuser of the nose sensor 200 can be performed through a light diffusion layer on or proximate to the emitter 210 structure.

The size and/or shape of the diffuser can help to avoid edge effects. For example, the thickness and/or diameter of the diffuser can help to avoid edge effects. Similarly, the proximity of the diffuser relative to the emitter 210 can help to avoid edge effects. Such configurations can advantageously help to desensitize the nose sensor 200 to geometric variability. For example, the size and/or shape of the diffuser and/or the positioning of the diffuser can allow the nose sensor 200 to accommodate various nose shapes and/or sizes, and/or accurately measure a patient's physiological parameters when light is emitted from the emitter 210, diffused by the diffuser, transmitted through a portion of the patient's body, and detected by the detector 212.

As shown in at least FIGS. 2-3 and 7-8, the nose sensor 200 can include an emitter 210. The emitter 210 can be coupled to a third post 205C of the outer prong 204. The third post 205C can be formed with or integral with the first post 205A, the second post 205B, and/or the outer prong 204. Alternatively, the third post 205C can be separate from or not integral with the first post 205A, the second post 205B, and/or the outer prong 204. The third post 205C can be configured to be inserted into a portion of the outer prong 204. For example, the third post 205C can be inserted into an aperture (not shown) along the outer prong 204. The third post 205C can be configured to be secured to the outer prong 204 or other portion of the nose sensor 200 via an adhesive, fastener, or another securement method. The third post 205C can form a flap. The flap can be rigid or substantially rigid. Alternatively, the flap can be flexible. The flap can be flexible relative to the first and/or second outer posts 205A, 205B, which can be substantially rigid. As shown in at least FIGS. 7 and 8, the flap can be pulled, bent, and/or peeled away from a patient's nose 207 in use. In use, the emitter 210 can be secured to an outer surface of the patient's nose 207, as described below. Alternatively, in use, the emitter 210 can be secured to an inner surface of the patient's nose 207. In some alternative configurations, the nose sensor 200 does not include a third post 205C. For example, the nose sensor 200 can have an inner prong 202 including an inner post 203 and a detector 212, and an outer prong 204 with a first post 205 a second post 205B, and a coupling portion 220. Such a configuration for a nose sensor 200 can be used alongside a separate emitter which can attach to an inside or outside portion of a patient's nose to interact with the detector 212 of nose sensor 200. Such an emitter can be electronically coupled to the detector 212 through wiring or a flexible circuit.

As discussed above, the third post 205C can form a flap. The emitter 210 can be coupled with the flap. For example, the emitter 210 can be coupled with an end of the flap. The emitter 210 can be positioned on an inner and/or outer surface of the flap. The flap configuration can advantageously allow the nose sensor 200 to accommodate various nose geometries. For example, the flap can allow the emitter 210 to be positioned approximately parallel to the detector 212 in use. In use, the emitter 210 can be positioned such that the emitter 210 remains in alignment with the detector 212 as the nose sensor 200 is attached to a patient. Thus, the emitter can remain in alignment with the detector 212 regardless of the shape and/or size of the patient's nose. In some alternative designs, the third post 205C can have a length that is different than the length of the inner post 203. For example, the third post 205C can have a shorter length than the length of the inner post 203. Alternatively, the third post 205C can have a greater length than the length of the inner post 203. A nose sensor 200 having an inner post 203 with a different length than the third post 205 can allow an emitter 210 coupled to the third post 205C to be offset or not aligned with a detector 212 coupled to the inner post 203. Such an offset can advantageously increase the path length between the emitter 210 and the detector 212. For example, such an offset can advantageously allow for light emitted from the emitter 210 to have to pass through more tissue before arriving and being detected by the detector 212. Even though misalignment between the emitter 210 and the detector 212 may result more scattering of light emitted from the emitter 210 and less emitted light getting to the detector 212, the misalignment and resulting increase in path length can advantageously allow light to pass through more body tissue, which can result in more accurate measurement of physiological parameters.

The emitter 210 and/or the detector 212 can be spaced away from the intermediate region of the outer prong 204 and/or the inner prong 202, or other region of the inner prong 202 and/or the outer prong 204 that contacts the patient's tissue. This can help to space the measurement location, for example the space between the emitter 210 and the detector 212, from the points, areas, and/or regions where the nose sensor 200 or portions thereof are secured to and/or contacting the patient. Spacing the measurement location from these securement locations can help to reduce false and/or inaccurate readings of physiological parameters such as those discussed herein. For example, a pressure region created by contact between the nose sensor 200 or portions thereof and the patient's tissue at and/or proximate to these securement locations may alter blood flow in the patient's tissue or otherwise affect the values of physiological parameters measured by the nose sensor 200. Thus, by spacing the emitter 210 and/or the detector 212 from points, areas, and/or regions where the nose sensor 200 or portions thereof are secured to and/or contacting the patient, the nose sensor 200 can allow for more accurate measurements of physiological parameters. As discussed above, the third post 205C can be coupled with an emitter 210. The third post 205C can be flexible. The third post 205C can apply little or no pressure on a patient's nose when the third post 205C and/or the emitter 210 is secured to an inside or outside portion of a patient's nose. For example, the emitter 210 can be coupled to the third post 205C and the emitter 210 can have an adhesive surrounding the emitter 210 that helps secure the emitter 210 and/or the third post 205C to an inside or outside portions of a patient's nose. In such configuration, the third post 205C and/or the emitter 210 can advantageously apply little or no pressure to the patient's nose, which can allow for more accurate measurements of physiological parameters.

An open side of the emitter 210 (for example, the side configured to face the patient's tissue) can be secured to and/or positioned against an outside surface of the patient's nose. The emitter 210 and/or the detector 212 can be secured to the patient's nose before, during, and/or after securement of the outer prong 204 and/or the inner prong 202 to the patient's nose. The outer prong 204 and/or the inner prong 202 can be secured to the patient's nose before, during, and/or after the emitter 210 and/or the detector 212 is secured to the patient's nose. For example, the emitter 210 can be placed approximately aligned with the detector 212 along an outer surface of the patient's nose 207. Alternatively, the emitter 210 can be placed approximately aligned with the detector 212 along an inner surface of the patient's nose 207.

The emitter 210 can include an adhesive that can be configured to couple the emitter 210 with the patient's nose. For example, the adhesive can secure the emitter 210 to the patient's nose at a position approximately aligned with the detector 212. The emitter 210 can include a liner. The liner can cover the emitter 210 when the emitter 210 is not in use. The liner can help to prevent the emitter 210 from inadvertently adhering to another object. The liner can help to keep the emitter 210 clean. The liner can help to maintain the adhesive properties of the adhesive backing of the emitter 210 and prevent errant readings due to detection of light before the nose sensor 200 is in place. To secure the emitter 210 to the patient, the liner can be removed.

The nose sensor 200 can include a lens on and/or around the detector 212. This lens can advantageously help focus light into the detector 212. For example, the lens can help focus light transmitted through a portion of a patient's body, such as a nose, and originating from the emitter 210. The lens can comprise various materials. For example, the lens can comprise glass and/or plastic. The lens can also comprise various optical refractive properties. For example, the lens can vary in thickness, curvature, refractive index, focal length, and/or other properties. The lens can be a simple lens. For example, the lens can comprise a single piece of transparent material. Alternatively, the lens can be a compound lens. For example, the lens can comprise one or more simple lenses arranged about a common axis. For example, the lens can comprise two or more, three or more, four or more, five or more, or six or more simple lenses arranged about a common axis. The lens can be paired with a diffuser to even out light distribution before detection and/or be surrounded by a black or dark colored border in order to block ambient stray light.

The nose sensor 200 can include wiring or a flexible circuit for electronically coupling the emitter 210 and the detector 212. The nose sensor 200 can include wiring or a flexible circuit that couples the emitter 210 and the detector 212 and that is positioned within a portion of the nose sensor 200. For example, the nose sensor 200 can including wiring or a flexible circuit that connects to the emitter 210 in an interior portion of the third post 205C and that travels through an interior portions of the outer prong 204, coupling portion 220, and/or inner post 203 to connect to the detector 212. In such configurations, the wiring or flexible circuit can be configured to fit within interior portions of the outer prong 204, coupling portion 220, and/or inner post 203 of nose sensor 200. This can advantageously simplify the attachment and/or securement of the nose sensor 200. Alternatively, in some configurations, the wiring or flexible circuit can be configured to be outside of interior portions of the nose sensor 200. For example, the emitter 210 can be electronically coupled to the detector 212 by wiring or a flexible circuit that travels outside the nose sensor 200 or components of the nose sensor 200. The nose sensor 200 can have an emitter 210 and no third post 205C. For example, the nose sensor 200 can have a detector 212 connected to a flexible circuit on one end of the flexible circuit and can have the other end of the flexible circuit connected to the emitter 210. For example, the flexible circuit can connect to the detector 212 at an end of the inner post 203, pass through an interior portion of the inner post 203, inner prong 202, coupling portion 220, and/or an opening in the outer prong 204 (not shown) and connect to the emitter 210. Thus, a portion of the flexible circuit can be confined or secured within an interior portion of the nose sensor 200 and a portion of the flexible circuit connected to the emitter 210 can be freely moveable outside the nose sensor 200 and can be secured to a portion of a patient's nose, such as an exterior portion.

FIGS. 9-15 illustrate a nose sensor 300. The nose sensor 300 can be similar to or identical to the nose sensor discussed above in some or many respects. As shown in FIGS. 9-15, the nose sensor 300 can include an inner prong 302 and an outer prong 304, which can be respectively similar to the inner prong 202 and the outer prong 204 described above in connection with the nose sensor 200 in some or many respects. The nose sensor 300 can include any one, or any combination, of features of the nose sensor 200.

For example, the nose sensor 300 can include an emitter and/or a detector similar to the emitter 210 and the detector 212 of the nose sensor 200.

For example, the inner prong 302 and the outer prong 304 can be coupled by a coupling portion 320. The coupling portion 320 can be generally rounded. The coupling portion 320 can be square, rectangular, and/or triangular. The coupling portion 320 can comprise a combination of these styles and/or shapes. The coupling portion 320 can help to maintain the rigidity of the sensor 300. The coupling portion 320 can bias the outer prong 304 towards the inner prong 302 and/or the inner prong 302 towards the outer prong 304. The coupling portion 320 can bias the outer prong 304 towards the inner prong 302 and/or the inner prong 302 towards the outer prong 304. The coupling portion 320 can space the outer prong 304 from the inner prong 302 to accommodate various nose geometries.

The inner prong 302 and the outer prong 304 can be integrally formed. The inner prong 302, outer prong 304, and/or the coupling portion 320 can be integrally formed. The inner prong 302 and/or the outer prong 304 can be formed separately and/or can be connected by the coupling portion 320. Additionally, the outer prong 304 and/or the inner prong 302 can be adhered, bonded, formed with, and/or otherwise connected to the coupling portion 320. The outer prong 304 and/or the inner prong 302 can connect to the coupling portion 320 by a snap-fit connection. For example, the outer prong 304 can snap into and thereby secure to the coupling portion 320, and/or the coupling portion 320 can snap into and thereby secure to the outer prong 304. The inner prong 302 can snap into and thereby secure to the coupling portion 320, and/or the coupling portion 320 can snap into and thereby secure to the inner prong 302.

The inner prong 302 can extend away from the outer prong 304. The inner prong 302 can extend away from the coupling portion 320 in a first and/or second direction. The inner prong 302 can include a detector as described in more detail below. At least a portion of the inner prong 302 can be configured to be positioned within a patient's nose. At least a portion of the inner prong 302 can be positioned adjacent an inner surface of a patient's nose. At least a portion of the inner prong 302 can engage at least a portion of an inner surface of a patient's nose. At least a portion of the inner prong 302 can be positioned within a patient's nose and/or at least a portion of the inner prong 302 can remain outside of the patient's nose when the nose sensor 300 is in use. Alternatively, at least a portion of the inner prong 302 can be configured to be positioned outside a patient's nose. At least a portion of the inner prong 302 can be positioned adjacent an outer surface of a patient's nose. At least a portion of the inner prong 302 can engage at least a portion of an outer surface of a patient's nose.

Figure 9:
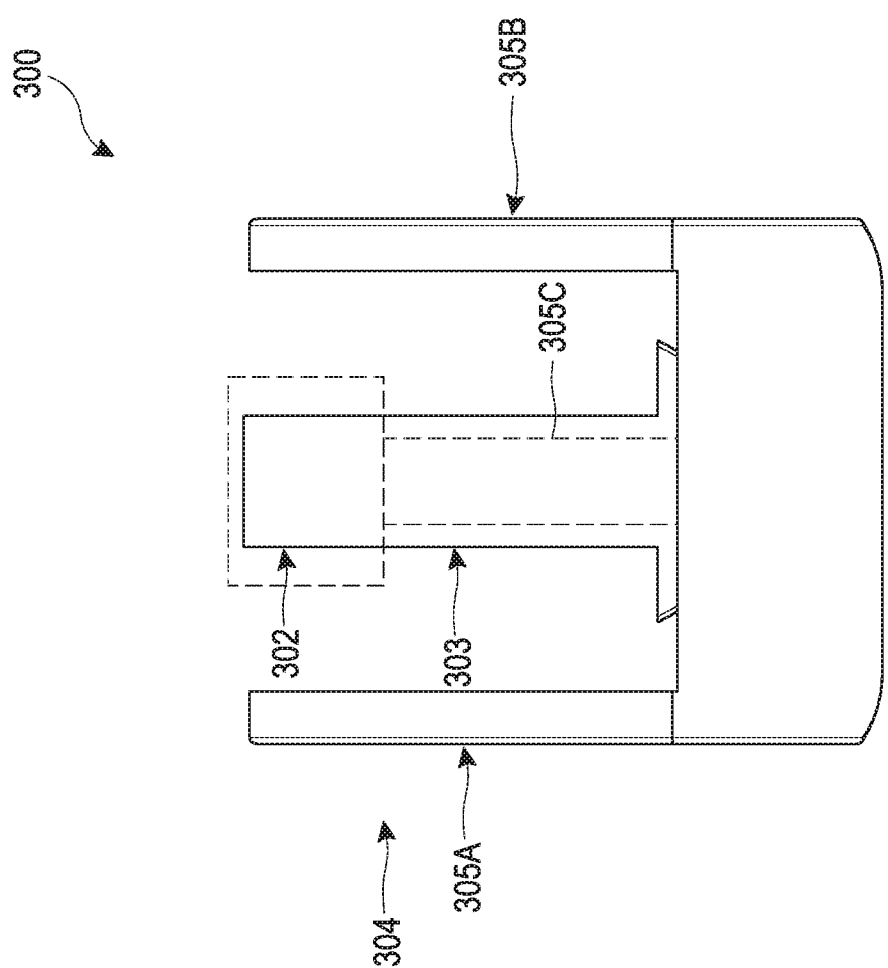
FIG. 9 illustrates a front view of a nose sensor.
Figure 10:
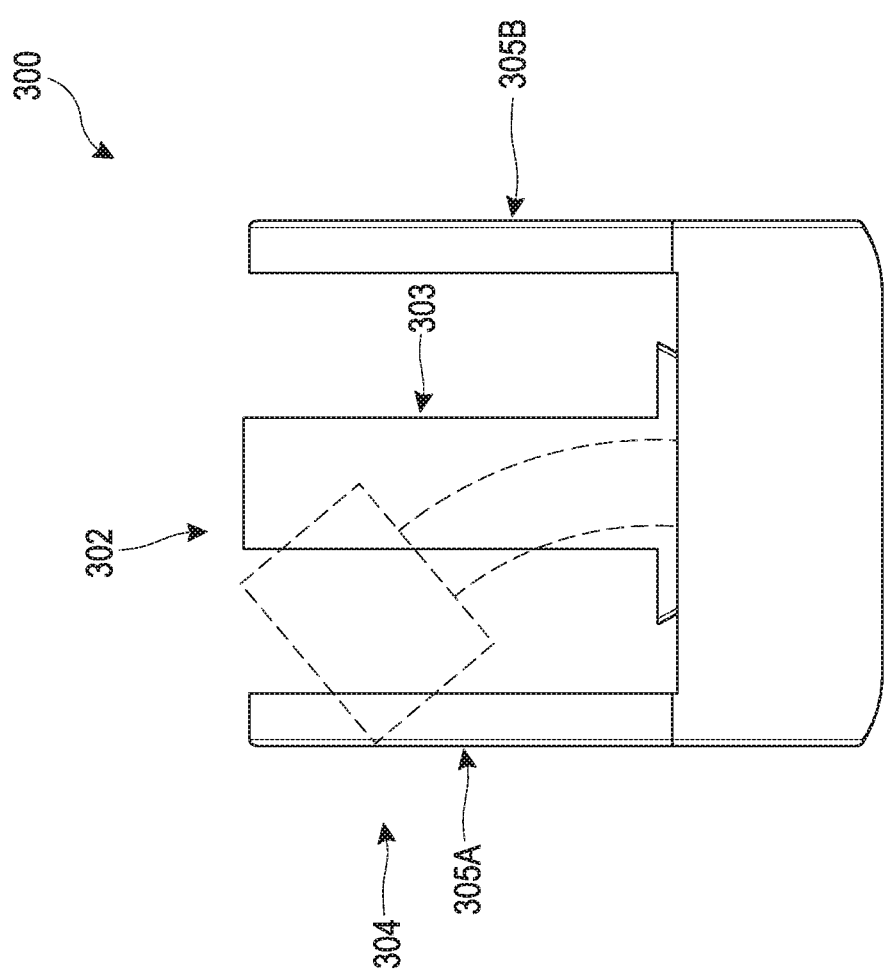
FIG. 10 illustrates a front view of the nose sensor of FIG. 9.
Figure 11:
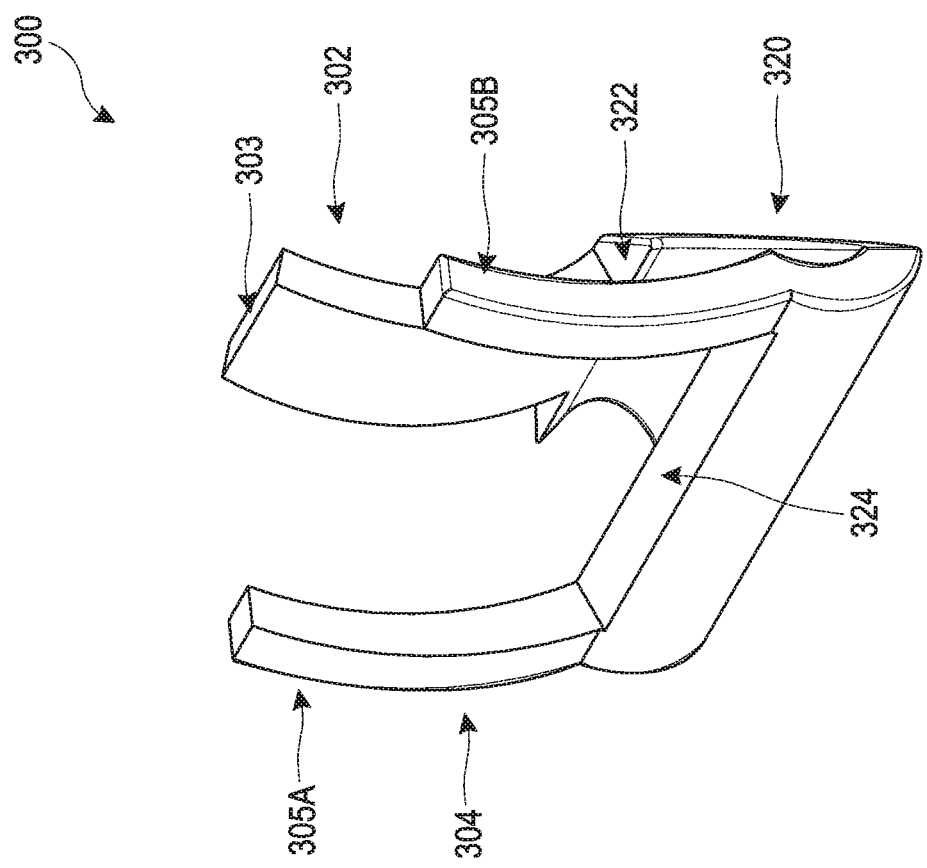
FIG. 11 illustrates a perspective view of the nose sensor of FIG. 9.
Figure 12:
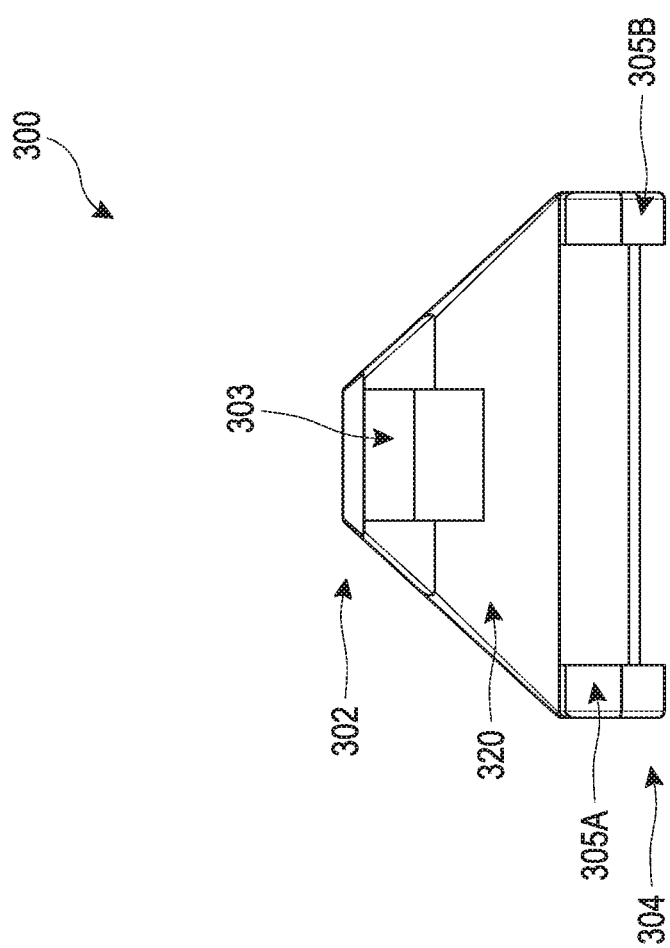
FIG. 12 illustrates a top view of the nose sensor of FIG. 9.
Figure 13:
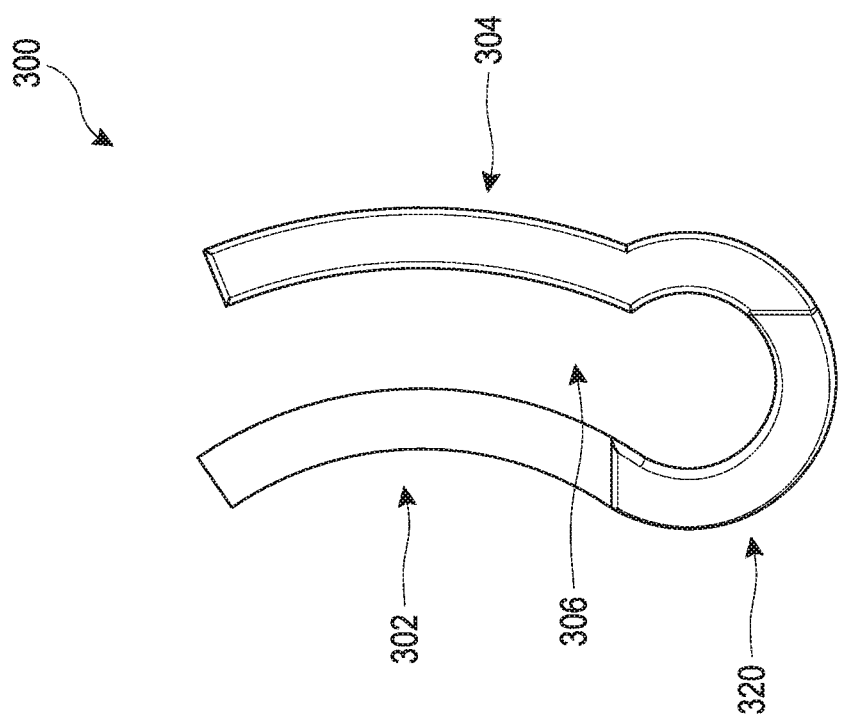
FIG. 13 illustrates a side view of the nose sensor of FIG. 9.
Figure 14:
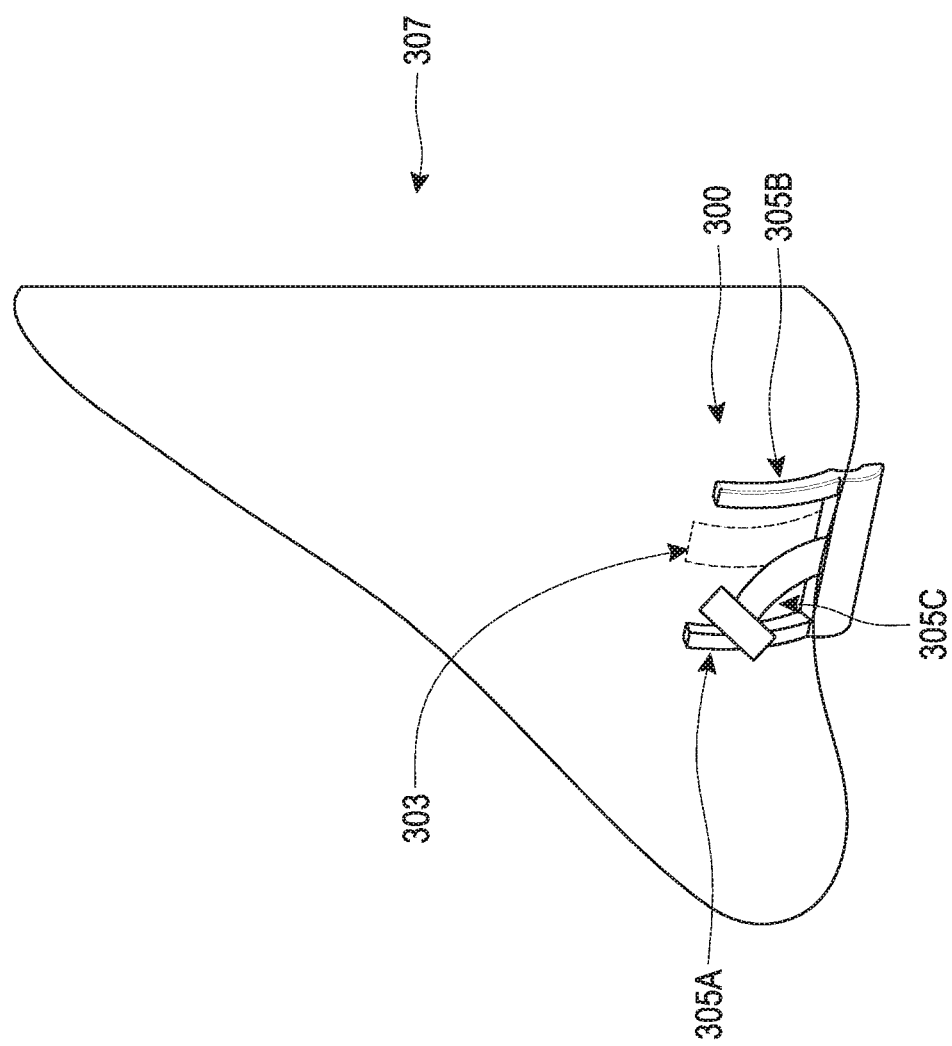
FIG. 14 illustrates a perspective view of the nose sensor of FIG. 9 in use.
Figure 15:
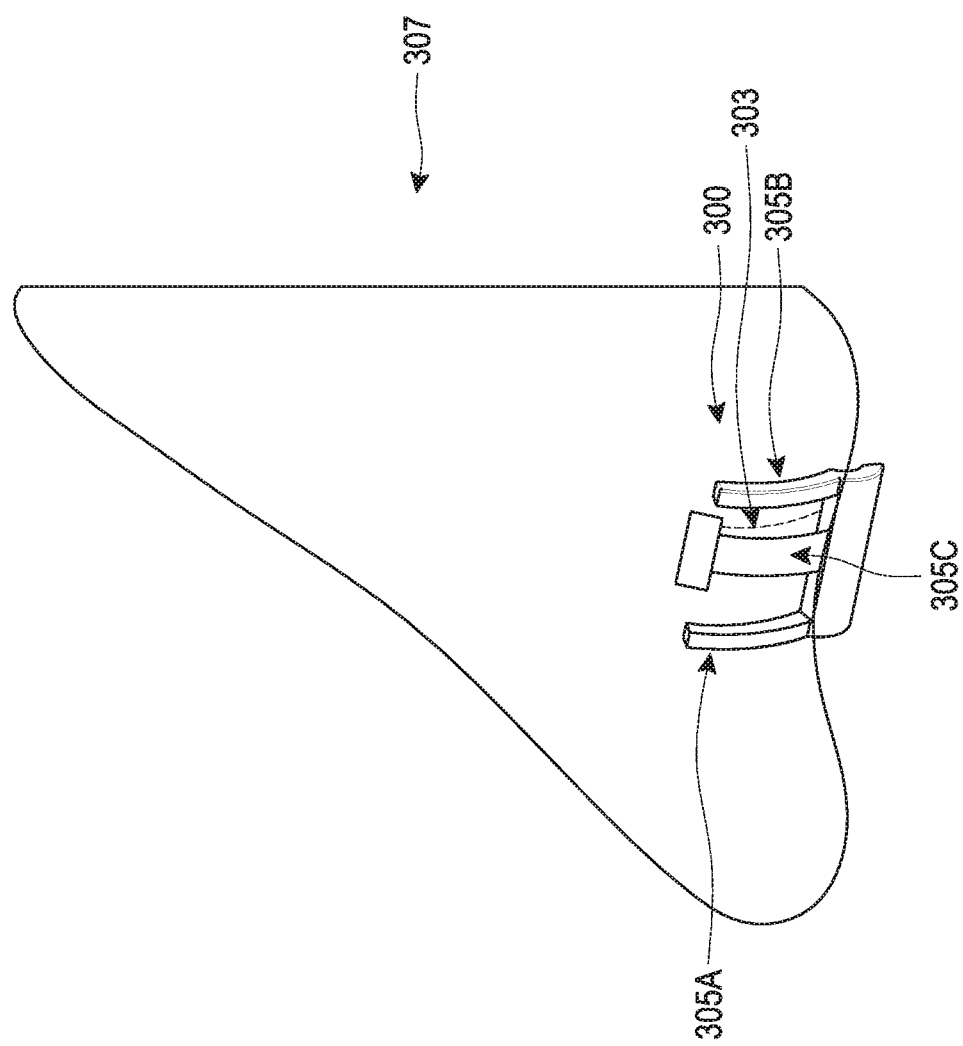
FIG. 15 illustrates a perspective view of the nose sensor of FIG. 9 in use.

As shown in FIGS. 9-15, the outer prong 304, outer posts 305A, 305B, 305C, the inner prong 302 and/or the inner post 303 can be curved. The curvature of the outer prong 304, outer posts 305A, 305B, 305C, the inner prong 302 and/or the inner post 303 can help to conform to the shape of the patient's nose. This can help to accommodate a variety of nasal geometries and/or can be more comfortable to the user. The outer prong 304, outer posts 305A, 305B, 305C, the inner prong 302 and/or the inner post 303 can be generally straight such that the outer prong 304 and/or outer posts 305A, 305B, 305C, and inner prong 302 and/or inner post 303 extend outwardly from the outer base 324, inner base 322, and/or the coupling portion 320. For example, as shown in FIG. 11, the outer posts 305A and 305B can be curved along a radius of curvature and in a direction similar to a curvature and direction of the inner prong 302 and/or inner post 303. As can be seen by FIGS. 14 and 15, this curvature and direction can advantageously allow the nose sensor 303 to secure to a patient's nose and also accommodate various shapes and/or sizes of noses of patient's while maintaining patient comfort. This similar curvature and direction of curvature can also allow the emitter coupled to an outer post 305C to align or substantially align with a detector coupled to the inner post 303.

The outer prong 304 can be approximately parallel to the inner prong 302. This can help to maintain an alignment between the emitter and detector in use.

As shown, the inner prong 302 can include an inner post 303 and/or an inner base 322. The inner post 303 can be coupled with the detector as discussed in more detail below. Thus, the inner post 303 can be configured to be positioned within the patient's nose, as discussed above. The inner base 322 can be coupled to and/or formed with the coupling portion 320 at one side and to the inner post 303 at the other side. The inner base 322 can be wider than the inner post 303. The inner base 322 can be generally trapezoidal. For example, an outer surface of the inner base 322 can have a width that is shorter than a width of an inner surface of the base 322. The inner base 322 can be square, rectangular, circular, and/or oval-shaped. The inner base 322 can also comprise other polygonal shapes, such as pentagonal, hexagonal, heptagonal, octagonal, nonagonal, decagonal, or otherwise shaped.

The inner post 303 can extend from the inner base 322. For example, the inner post 303 can extend upwardly from the inner base 322. The inner post 303 can be positioned at approximately the center of the inner base 322. Alternatively, the inner post 303 can be positioned in a non-centered location of the inner base 322, for example, on a location of the inner base 322 that is closer to an edge of the inner base 322.

As shown in at least FIGS. 11 and 15, the outer prong 304 can include one or more outer posts 305. For example, the outer prong 304 can include one or more, two or more, three or more, four or more, five or more, or six or more outer posts 305. The outer prong 304 can include outer posts 305A, 305B, 305C and an outer base 324. The outer base 324 can be coupled to and/or formed with the coupling portion 320 at one side and/or to the outer posts 305A, 305B, and/or 305C at the other side. The outer posts 305A, 305B can be spaced apart along the outer base 324. For example, the outer posts 305A, 305B can be spaced apart along a top portion of the outer base 324. The outer posts 305A, 305B, and/or 305C can extend perpendicular from a top surface of the outer base 324. Alternatively, the outer posts 305A, 305B, and/or 305C can extend at an angle that is not perpendicular from a top surface of the outer base 324.

The outer posts 305A, 305B, and/or 305C can have the same and/or varying widths and/or lengths. The outer posts 305A, 305B, and/or 305C can have widths and the inner post 303 can have a width. The width of the inner post 303 can be wider than the respective widths of the outer posts 305A, 305B, and/or 305C. This can help to secure the nose sensor 300 to the patient's nose. The nose sensor 300 can have a reduced profile and/or incorporate reduced material, thereby reducing the overall bulkiness of the nose sensor 300. Thus, the nose sensor 300 can be more comfortable to the patient.

As discussed above, the nose sensor 300 can include an emitter. The emitter can be coupled to the outer post 305C of the outer prong 304. The outer post 305C can be formed or integral with the outer post 305A, the outer post 305B, and/or the outer prong 304. Alternatively, the outer post 305C can be separate from or not integral with the outer post 305A, the outer post 305B, and/or the outer prong 304. The outer post 305C can be configured to be inserted into a portion of the outer prong 304. For example, outer post 305C can be inserted into an aperture (not shown) along the outer prong 304 and/or outer base 324. The outer post 305C can be configured to be secured to the outer prong 304, outer base 324, or other portion of the nose sensor 300 via an adhesive, fastener, or another securement method. As shown in at least FIGS. 14 and 15, the outer post 305C can form a flap. The flap can be rigid or substantially rigid. Alternatively, the flap can be flexible. The flap can be flexible relative to the outer posts 305A, 305B, which can be substantially rigid. As shown in at least FIGS. 14 and 15, the flap can be pulled, bent, and/or peeled away from a patient's nose 307 in use. In use, the emitter can be secured to an outer surface of the patient's nose 307, as described below. Alternatively, in use, the emitter can be secured to an inner surface of the patient's nose 307. In some alternative configurations, the nose sensor 300 does not include an outer post 305C. For example, the nose sensor 300 can have an inner prong 302 including an inner post 303 and a detector 312, and an outer prong 304 with an outer post 305A, an outer post 305B, an outer base 324, and a coupling portion 320. Such a configuration for a nose sensor 300 can be used alongside a separate emitter which can attach to an inside or outside portion of a patient's nose to interact with the detector of nose sensor 300. Such an emitter can be electronically coupled to the detector through wiring or a flexible circuit.

As discussed above, the emitter of nose sensor 300 can be coupled with the outer post 305C which can comprise a flap. For example, the emitter can be coupled with an end of the flap. The emitter can be positioned on an inner and/or outer surface of the flap. The flap configuration can advantageously allow the nose sensor 300 to accommodate various nose geometries. For example, the flap can allow the emitter to be positioned approximately parallel to the detector in use. In use, the emitter can be positioned such that the emitter remains in alignment with the detector as the nose sensor 300 is attached to a patient. Thus, the emitter can remain in alignment with the detector regardless of the shape and/or size of the patient's nose. In some alternative designs, the outer post 305C can have a length that is different than the length of the inner post 303. For example, the outer post 305C can have a shorter length than the length of the inner post 303. Alternatively, the outer post 305C can have a greater length than the length of the inner post 303. A nose sensor 300 having an inner post 303 with a different length than the outer post 305C can allow an emitter coupled to the outer post 305C to be offset or not aligned with a detector coupled to the inner post 303. Such an offset can advantageously increase the path length between the emitter and the detector. For example, such an offset can advantageously allow for light emitted from the emitter to have to pass through more tissue before arriving and being detected by the detector. Even though misalignment between the emitter and the detector may result more scattering of light emitted from the emitter and less emitted light getting to the detector, the misalignment and resulting increase in path length can advantageously allow light to pass through more body tissue, which can result in more accurate measurement of physiological parameters.

The outer prong 304 and the outer posts 305A, 305B, 305C of the outer prong 304, the coupling portion 320, and/or the inner prong 302 can comprise various lengths. The outer prong 304 and/or the outer posts of the outer prong 304 can be longer than the inner prong 302 and/or the coupling portion 320. The outer prong 304 and/or the outer posts of the outer prong 304 can be shorter than the inner prong 302 and/or the coupling portion 320. Thus, the outer prong 304, coupling portion 320, and/or the inner prong 302 can comprise various lengths so as to aid securement to patient's having varying sizes and/or shapes of noses. The outer prong 304, the coupling portion 320, and/or the inner prong 302 can also comprise various lengths so as to aid comfort to patient's having varying sizes and/or shapes of noses when the nose sensor 300 or a portion thereof is attached to the patient.

The outer posts 305A, 305B, 305C can extend outwardly from the outer base 324. The outer posts 305A, 305B, 305C can be curved as the outer posts 305A, 305B, 305C extend away from the outer base 324. For example, a lower portion of the outer posts 305A, 305B, 305C can be generally curved. An upper portion of the outer posts 305A, 305B, 305C can extend generally upwardly from the lower portion. The upper portion of the outer posts 305A, 305B, 305C can extend inwardly towards one another and/or towards a coupling region 306 (see FIG. 13). The upper portion of the outer posts 305A, 305B, 305C can curve in the same direction, such as is shown in FIG. 13. This curvature can advantageously help the nose sensor 300 conform more comfortably to a patient's nose or a portion thereof. The outer base 324 can be coupled to and/or formed with the coupling portion 320 at one side and to the outer prong 304 at the other side. The outer base 324 can be coupled to and/or formed with the coupling portion 320 at one side and to the outer post 305A, 305B, and/or 305C at the other side. The outer base 324 can be wider than the outer post 305A, 305B, and/or 305C. The outer base 324 can be generally trapezoidal. For example, an outer surface of the outer base 324 can have a width that is shorter than a width of an inner surface of the outer base 324. The outer base 324 can be square, rectangular, circular, and/or oval-shaped. The outer base 324 can also comprise other polygonal shapes, such as pentagonal, hexagonal, heptagonal, octagonal, nonagonal, decagonal, or otherwise shaped.

The outer prong 304, outer posts 305A, 305B, and 305C, the inner post 303, inner base 322, outer base 324, and/or the coupling portion 320 can comprise a cross-section that is circular. Alternatively, the outer prong 304, outer posts 305A, 305B, and 305C, the inner post 303, inner base 322, outer base 324, and/or the coupling portion 320 can comprise a cross-section that is non-circular. For example, the outer prong 304, outer posts 305A, 305B, and 305C, the inner post 303, inner base 322, outer base 324, and/or the coupling portion 320 can comprise a cross-section that is polygonal. The outer prong 304, outer posts 305A, 305B, and 305C, the inner post 303, inner base 322, outer base 324, and/or the coupling portion 320 can comprise a cross-section that is triangle, quadrilateral, pentagonal, hexagonal, heptagonal, octagonal, nonagonal, decagonal, or otherwise shaped. The outer prong 304, outer posts 305A, 305B, and 305C, the inner post 303, inner base 322, outer base 324, and/or the coupling portion 320 can comprise a cross-section that is some combination of these circular and/or polygonal shapes. For example, the outer prong 304, outer posts 305A, 305B, and 305C, the inner post 303, inner base 322, outer base 324, and/or the coupling portion 320 can comprise a cross-section that is partially circular and partially polygonal. As shown in at least FIGS. 11 and 15, the outer posts 305A and 305B can comprise a cross section that is square shaped and the outer posts 305A and 305B can be curved along their length to better accommodate various nose sizes and/or shapes. As also shown in at least FIGS. 11 and 15, the inner post 303 can comprise a rectangular shape and can have a cross sectional width that is larger than the cross sectional width of the outer post 305A and/or the outer post 305B, which can aid securement of the inner post 303 to an interior portion of a patient's nose or an exterior portion of the patient's nose when the nose sensor 303 is secured to the patient. As also shown in at least FIGS. 11 and 15, the outer base 324 can have a rectangular cross section and can be curved along its length, which can help to accommodate various nose sizes and/or shapes in the region where the outer base 324 is secured or proximate to a portion of a patient's nose when the nose sensor 303 is secured to the patient. As also shown in at least FIGS. 11 and 15, the coupling portion 320 can comprise a quadrilateral shape where a back side of the coupling portion 320 (proximate to the inner base 322) has a width that is smaller than a front side of the coupling portion 320 (proximate to the outer base 324). This shape of the coupling portion can advantageously maintain the spacing of the outer posts 305A and 305B along the outer base 324 while also minimizing the amount of material and/or weight of the nose sensor 303 by having right and left sides of the coupling portion extend partially toward one another to culminate in the back side of the coupling portion 320 near the inner base 322.

Similar to the nose sensor 200, the outer prong 304 and/or the outer posts 305A, 305B, 305C of nose sensor 300 can be curved at an intermediate portion. The intermediate portion of the outer prong 304 and/or of the outer posts 305A, 305B, 305C can be curved towards the inner prong 302 and/or inner port 303. The intermediate portion of the outer prong 304 and/or the outer posts 305A, 305B, 305C can be generally straight such that the outer prong 304 extends generally upwardly and/or parallel to the inner prong 302 and/or the inner post 303. The shape of the outer prong 304, outer posts 305A, 305B, 305C, the inner prong 302 and/or inner post 303 can beneficially help to secure the nose sensor 300 to the patient's nose. For example, the shape of the outer prong 304 or outer post 305A, 305B, 305C relative to the shape of the inner prong 302 and/or the inner post 303 can help to secure the nose sensor 300 to the patient's nose and can accommodate various nose sizes and/or shapes.

FIGS. 14 and 15 illustrate the nose sensor 300 when secured to the nose of a patient. As shown, at least a portion of the inner post 303 can slide into the patient's nose and engage an inner surface of the patient's nose. At least a portion of the outer posts 305A, 305B, 305C can slide along an outer region of the patient's nose and engage an outer surface of the patient's nose. Alternatively, at least a portion of the inner post 303 can slide along an outer region of the patient's nose and engage an outer surface of the patient's nose, and at least a portion of the outer posts 305A, 305B, 305C can slide into the patient's nose and engage an inner surface of the patient's nose. These configurations can help to ensure that the nose sensor 300 remains secured to the patient's nose and/or is comfortable when secured to the patient. These configurations can help to allow the nose sensor 300 to sit flush against the patient's tissue, inside and/or outside of the patient's nose. The sensor 300 may be less bulky and/or occupy less space on the patient's tissue. For example, as shown in FIG. 9, a central longitudinal axis of the inner post 303 can be aligned with or parallel to a central longitudinal axis of the inner prong 202. As also shown in FIG. 9, a central longitudinal axis of the inner post 303 can be aligned with a central longitudinal axis of the outer post 305C, which can help ensure that the emitter and the detector are aligned to accurately measure physiological parameters when the nose sensor 300 is in us. The outer post 305A can be spaced from the outer post 305B. For example, the outer post 305A can have a side wall that is positioned adjacent a first side wall of the outer prong 304 and the second outer post 305B can have a side wall that is positioned adjacent a second side wall of the outer prong 304.

As illustrated in at least FIGS. 9-11, the inner post 303 can include a first side wall and a second side wall. The outer post 205A and/or the outer post 205B can be spaced laterally away from one another along the outer prong 304 and/or the outer base 324. The outer post 305A can be positioned laterally outward from the first side wall of the inner post 303. The outer post 305B can be positioned laterally outward from the second side wall of the inner post 303.

The inner post 303 can apply pressure to an inner portion of the nose of the patient when the nose sensor 300 is secured to at least a portion of the patient's nose. The outer post 305A can apply pressure to a portion of the nose of the patient that can be spaced laterally outwardly from at least a portion of the inner portion of the patient's nose where the inner post 303 applies a pressure when the nose sensor 300 is secured to the patient. The outer post 305B can apply pressure to a portion of the nose of the patient that can be spaced laterally outwardly from the inner portion of the patient's nose where the inner post 303 applies a pressure when the nose sensor 300 is secured to the patient. The inner post 303 can apply pressure to a portion of the nose of the patient, as discussed above. The portion of the nose of the patient can be positioned between the outer post 305A and/or the outer post 305B when the inner prong 302 and the outer prong 304 of the nose sensor 300 are secured to the patient. The inner post 303 of the inner prong 302 can apply pressure to a portion of the nose of the patient. The portion of the nose of the patient can be positioned between the outer post 305A and the outer post 305B when the inner prong 302 and the outer prong 304 are secured to the patient.

To secure the nose sensor 300 to the patient, the inner post 303 can apply pressure to an inner surface of the patient's nose, as discussed above. For example, the inner post 303 can apply pressure from the inside of the patient's nose towards the outside of the patient's nose. The outer post 305A and/or the outer post 305B can apply pressure to the outer surface of the patient's nose. For example, the outer post 205A and/or the outer post 205B can apply pressure from the outside of the patient's nose towards the inside of the patient's nose. The inner post 303 can apply pressure to a portion of the patient's nose that is positioned at least partially between the outer posts 305A, 305B. The outer posts 305A, 305B can apply pressure to a portion of the patient's nose that is positioned at least partially outwardly from the inner post 303.

As discussed above, the positioning of the inner prong 302 and/or the outer prong 304 of the nose sensor 300 can advantageously help to secure the nose sensor 300 to the patient while also minimizing the contact of portions of the nose sensor 300 with the patient. As also discussed above, varying the positioning of portions of the nose sensor 300 and/or minimizing the contact between portions of the nose sensor 300 and the patient can aid patient comfort and improve securement. For example, the inner prong 302 (or portions thereof), the outer prong 304 (or portions thereof), the coupling portion 220 (or portions thereof) can secure to the patient by contacting one or more points, areas, or portions of the patient's nose. For example, the inner prong 302 can contact an inner or outer portion of the patient's nose and the outer posts 305A, 305B of the outer prong 304 can contact a different inner or outer portion of the patient's nose when the nose sensor 300 is secured to the patient. Compared to other sensors which may contact a larger portion or region of a patient's nose when secured to the patient, the configuration of the inner prong 302 and/or outer prong 304 of the nose sensor 300 can contact less of a portion or region of a patient's nose when the nose sensor 300 is secured to a patient. As discussed above, the inner prong 302 and/or outer prong 304 of the nose sensor 300 can be configured to contact a minimal amount of a portion or region of a patient's nose when the nose sensor 300 is secured to a patient.

The nose sensor 300 can measure various physiological parameters of a patient, like those discussed above. As discussed above, the nose sensor 300 can include an emitter and a detector to allow the nose sensor 300 to measure the patient's physiological parameters, such as those discussed herein.

Various arrangements of the emitter and/or the detector can allow the nose sensor 300 to take more accurate measurements. The emitter can be a light-emitting diode (LED). The emitter can emit light of a certain wavelength. The light emitter can emit light of different wavelengths in sequence with only one emitter emitting light at a given time, thereby forming a pulse sequence. The number of emitters is not limiting and can range from two to eight, or more in some instances. Detailed descriptions and additional examples of the light emitters are provided in U.S. Pat. No. 9,277,880, referenced above.

The detector can detect light from the emitter after the light passes through and is attenuated by tissue of the patient's nose. For example, the detector can comprise photodetectors, photodiodes, phototransistors, and/or the like. Additional details of the photodetector are described in U.S. Pat. No. 9,277,880, referenced above. The detector can generate an electrical signal based on the detected light from the emitter. The signal of the detected light from the emitter can be input into a signal processor described herein, such that the signal processor can process an output of the sensor 300.

The detector can be positioned along the inner prong 302. For example, the detector can be coupled with an end of the inner post 303 of the inner prong 302. The detector can be coupled with an upper edge of the inner post 303. The detector can be coupled with an inner surface of the inner post 303. The detector can be adhered, bonded, formed into, and/or otherwise attached to the inner post 303. The detector can be configured to connect to the inner post 303 by a snap-fit connection. The inner post 303 and the detector can be integrally formed. The detector can be secured to an inner surface of the patient's tissue within the patient's nose. The detector and/or the emitter can advantageously assist in desensitizing the nose sensor 300 to various geometric variations.

The detector can be secured to the inner surface of the patient's nose by an adhesive. Alternatively, the detector can be secured to the inner surface of the patient's nose without adhesives. For example, the engagement of the outer prong 304 and/or the inner prong 302 with the patient's nose can hold the detector against the inner surface of the patient's nose without the use of adhesives.

The detector can be secured to the outer surface of the patient's nose by an adhesive. Alternatively, the detector can be secured to the outer surface of the patient's nose without adhesives. For example, the engagement of the outer prong 304 and/or the inner prong 302 with the patient's nose can hold the detector against the outer surface of the patient's nose without the use of adhesives.

The emitter can be secured to the inner surface of the patient's nose by an adhesive. Alternatively, the emitter can be secured to the inner surface of the patient's nose without adhesives. For example, the engagement of the outer prong 304 and/or the inner prong 202 with the patient's nose can hold the emitter against the inner surface of the patient's nose without the use of adhesives.

The emitter can be secured to the outer surface of the patient's nose by an adhesive. Alternatively, the emitter can be secured to the outer surface of the patient's nose without adhesives. For example, the engagement of the outer prong 304 and/or the inner prong 302 with the patient's nose can hold the emitter against the outer surface of the patient's nose without the use of adhesives. The emitter and/or the detector can include an adhesive layer and a release liner overtop the adhesive layer. The release liner can be removed when the emitter and/or the detector is ready to be secured to a patient's skins surface, such as an interior or exterior portion of a patient's nose.

The securement of the nose sensor 300 to the patient can be configured to maintain an alignment between the emitter and detector when the nose sensor 300 is in use, as discussed below. The detector can be angled away from the outer prong 304, the outer posts 305A, 305B, 305C and/or the emitter. The nose sensor 300 shape and/or size can be varied so as to reduce the bulkiness and/or the obtrusiveness of the nose sensor 300. Thus, the nose sensor 300 can maintain a generally low profile. The nose sensor 300 can include a diffuser positioned proximate to the emitter. For example, the diffuser can be positioned in front of the emitter. The diffuser can comprise silicone. For example, the diffuser can include white and/or black silicone to scatter a greater amount of light and/or more accurately measure a patient's physiological parameters. The diffuser can comprise materials other than silicone. For example, the diffuser can comprise acrylic and/or plastics such as polycarbonate and/or polycarbonate film or sheets. The diffuser can comprise glass such as opal glass, ground glass, patterned glass, and/or a combination of such materials. The diffuser can also comprise other materials with varying material properties and/or characteristics. The diffuser can comprise one or more layers with different material properties and/or characteristics. For example, the diffuser can comprise, two or more, three or more, four or more, five or more, six or more, seven or more, or eight or more layers with different material properties and/or characteristics. Additionally, the diffuser can comprise one or more layers with similar material properties and/or characteristics. For example, the diffuser can comprise, two or more, three or more, four or more, five or more, six or more, seven or more, or eight or more layers with similar material properties and/or characteristics.

The diffuser of the nose sensor 300 can diffuse emitted light prior to entering the tissue. The diffuser can advantageously spread out, disseminate, and/or scatter light exiting from the emitter into and/or around a portion of a patient's body, for example the nose. This can permit light originating from the emitter to pass through a wider region or area of a patient's body, and thus better facilitate collection of physiological parameters (such as those discussed above). The detector can be sized and shaped to receive the optical radiation after it attenuates through tissue and fluids of a portion of a body. Diffusing light prior to entering the tissue can be advantageous because the light is allowed to pass through more tissue. This allows the light to sample more of the body tissue before being detected. It also provides for more even and consistent light across a larger portion of tissue. The diffusion of light by the diffuser of the nose sensor 300 can be performed through a light diffusion layer on or proximate to the emitter structure.

The size and/or shape of the diffuser can help to avoid edge effects. For example, the thickness and/or diameter of the diffuser can help to avoid edge effects. Similarly, the proximity of the diffuser relative to the emitter can help to avoid edge effects. Such configurations can advantageously help to desensitize the nose sensor 300 to geometric variability. For example, the size and/or shape of the diffuser and/or the positioning of the diffuser can allow the nose sensor 300 to accommodate various nose shapes and/or sizes, and/or accurately measure a patient's physiological parameters when light is emitted from the emitter, diffused by the diffuser, transmitted through a portion of the patient's body, and detected by the detector.

The emitter and/or the detector can be spaced away from the intermediate region of the outer prong 304 and/or the inner prong 302, or other region of the inner prong 302 and/or the outer prong 304 that contacts the patient's tissue when the nose sensor 300 is secured to the patient. The emitter and/or the detector can be spaced away from the outer post 305A, 305B, 305C, the inner prong 302 and/or the inner post 303 that contacts the patient's tissue when the nose sensor 300 is secured to the patient. This can help to space the measurement location, for example the space between the emitter and the detector, from the points, areas, and/or regions where the nose sensor 300 or portions thereof are secured to and/or contacting the patient. Spacing the measurement location from these securement locations can help to reduce false and/or inaccurate readings of physiological parameters such as those discussed herein. For example, a pressure region created by contact between the nose sensor 300 or portions thereof and the patient's tissue at and/or proximate to these securement locations may alter blood flow in the patient's tissue or otherwise affect the values of physiological parameters measured by the nose sensor 300. Thus, by spacing the emitter and/or the detector from points, areas, and/or regions where the nose sensor 300 or portions thereof are secured to and/or contacting the patient, the nose sensor 300 can allow for more accurate measurements of physiological parameters. As discussed above, the outer post 305C can be coupled with an emitter. The outer post 305C can be flexible. The outer post 305C can apply little or no pressure on a patient's nose when the outer post 305C and/or the emitter is secured to an inside or outside portion of a patient's nose. For example, the emitter can be coupled to the outer post 305C and the emitter can have an adhesive which surrounds the emitter and secures the emitter and/or the outer post 305C to an inside or outside portion of a patient's nose. In such configuration, the outer post 305C and/or the emitter can advantageously apply little or no pressure to the patient's nose, which can allow for more accurate measurements of physiological parameters.

An open side of the emitter (for example, the side configured to face the patient's tissue) can be secured to and/or positioned against an outside surface of the patient's nose. The emitter and/or the detector can be secured to the patient's nose before, during, and/or after securement of the outer prong 304 and/or the inner prong 302 to the patient's nose. The outer prong 304 and/or the inner prong 302 can be secured to the patient's nose before the emitter and/or the detector is secured to the patient's nose. For example, the emitter can be placed approximately aligned with the detector along an outer surface of the patient's nose 307. Alternatively, the emitter can be placed approximately aligned with the detector along an inner surface of the patient's nose 307.

The emitter can include an adhesive that can be configured to couple the emitter with the patient's nose. For example, the adhesive can secure the emitter to the patient's nose at a position approximately aligned with the detector. The emitter can include a liner. The liner can cover the emitter when the emitter is not in use. The liner can help to prevent the emitter from inadvertently adhering to another object. The liner can help to keep the emitter clean. The liner can help to maintain the adhesive properties of the adhesive backing of the emitter and prevent errant readings due to detection of light before the nose sensor 300 is in place. To secure the emitter to the patient, the liner can be removed.

The nose sensor 300 can include a lens on and/or around the detector. This lens can advantageously help focus light into the detector. For example, the lens can help focus light transmitted through a portion of a patient's body, such as a nose, and originating from the emitter. The lens can comprise various materials. For example, the lens can comprise glass and/or plastic. The lens can also comprise various optical refractive properties. For example, the lens can vary in thickness, curvature, refractive index, focal length, and/or other properties. The lens can be a simple lens. For example, the lens can comprise a single piece of transparent material. Alternatively, the lens can be a compound lens. For example, the lens can comprise one or more simple lenses arranged about a common axis. For example, the lens can comprise two or more, three or more, four or more, five or more, or six or more simple lenses arranged about a common axis. The lens can be paired with a diffuser to even out light distribution before detection and/or be surrounded by a black or dark colored border in order to block ambient stray light.

The nose sensor 300 can include wiring or a flexible circuit for electronically coupling the emitter and the detector. The nose sensor 300 can include wiring or a flexible circuit that couples the emitter and the detector and that is positioned within a portion of the nose sensor 300. For example, the nose sensor can including wiring or a flexible circuit that connects to the emitter in an interior portion of the outer post 305C and that travels through an interior portions of the outer prong 304, outer base 324, coupling portion 320, and/or inner post 303 to connect to the detector. In such configurations, the wiring or flexible circuit can be configured to fit within interior portions of the outer prong 304, coupling portion3, and/or inner post 303 of nose sensor 300. This can advantageously simplify the attachment and/or securement of the nose sensor 300. Alternatively, in some configurations, the wiring or flexible circuit can be configured to be outside of interior portions of the nose sensor 300. For example, the emitter can be electronically coupled to the detector by wiring or a flexible circuit that travels outside the nose sensor 300 or components of the nose sensor 300. The nose sensor 300 can have an emitter and no outer post 305C. For example, the nose sensor 300 can have a detector connected to a flexible circuit on one end of the flexible circuit and can have the other end of the flexible circuit connected to the emitter. For example, the flexible circuit can connect to the detector at an end of the inner post 303, pass through an interior portion of the inner post 303, inner prong 302, inner base 322, coupling portion 320, outer base 324, and/or an opening in the outer base 324 (not shown) and/or outer prong 304 and connect to the emitter. Thus, a portion of the flexible circuit can be confined or secured within an interior portion of the nose sensor 300 and a portion of the flexible circuit connected to the emitter can be freely moveable outside the nose sensor 300 and can be secured to a portion of a patient's nose, such as an exterior portion.

FIGS. 16-22 illustrate a nose sensor 400. The nose sensor 400 is similar to or identical to the nose sensor discussed above in many respects. As shown in FIGS. 16-22, the nose sensor 400 can include an inner prong 402 and an outer prong 404, which can be respectively similar to the inner prong 202, 302 and the outer prong 204, 304 described above in connection with the nose sensor 200, 300. The nose sensor 400 can include any one, or any combination, of features of the nose sensor 200, 300.

The nose sensor 400 can include a clip-type arrangement. For example, the inner prong 402 and the outer prong 404 can be coupled by a coupling portion 420. The coupling portion 420 can form a joint 421. For example, the joint 421 can include a pivot pin 430. The inner prong 402 can include at least one pivot hole 432 and/or the outer prong 404 can include at least one pivot hole 434. The pivot pin 430 can be configured to pass through the pivot holes 432, 434 to pivotally connect the outer prong 404 with the inner prong 402.

Figure 16:
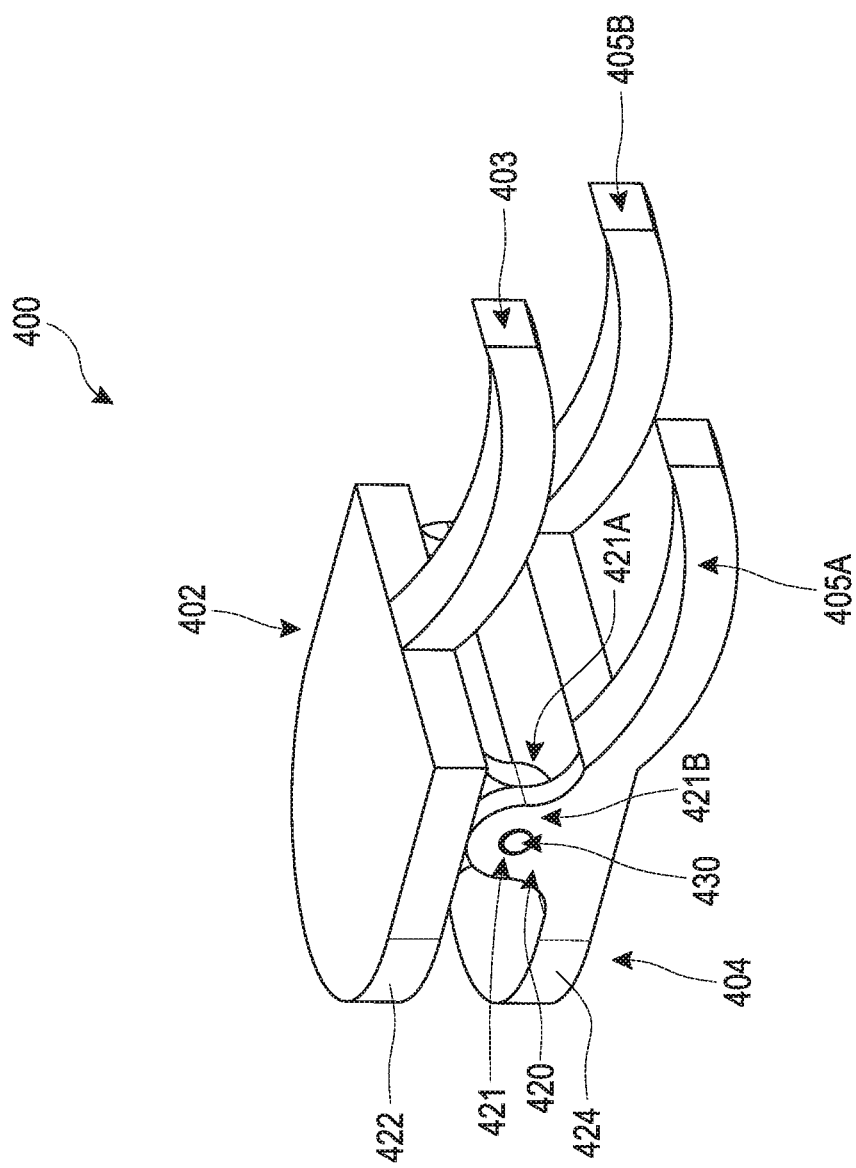
FIG. 16 illustrates a perspective view of a nose sensor.

The joint 421 can include one or more, two or more, three or more, four or more, or five or more joint portions. As shown in FIG. 16, the joint 421 can include an inner joint portion 421A and an outer joint portion 421B. The inner joint portion 421A can be coupled to and/or formed with the inner prong 402. The outer joint portion 421B can be coupled to and/or formed with the outer prong 404. As shown, the joint 421 can include at least two outer joint portions 421B and at least two inner joint portions 421A. The outer joint portions 421B can extend inwardly from the outer prong 404 and/or towards the inner prong 402 when assembled. The inner joint portions 421A can extend inwardly from the inner prong 402 and/or towards the outer prong 404 when assembled.

The outer joint portions 421B can be formed along opposite outer edges of the outer prong 404. This can allow the inner joint portions 421A to be positioned between the outer joint portions 421B. The inner joint portions 421A can form a single protrusion. The inner joint portions 421A can include two or more protrusions. As shown, the pivot pin 430 can extend through the outer joint portions 421B and the inner joint portions 421A when assembled.

The joint 421 can allow the outer prong 404 and/or the inner prong 402 to pivot with respect to one another. This can advantageously accommodate various shaped nasal geometries. This can also advantageously help a caregiver or other person to position and secure the nose sensor 400 to the nose of a patient.

As shown in FIGS. 16-22, the inner prong 402 can include an inner base 422 and an inner post 403. The inner post 403 can be formed or integral with inner base 422. The inner base 422 can have substantially flat inner and/or outer surfaces. At least one end of the inner base 422 can be rounded and/or squared. As shown in FIG. 16, one end of the inner base 422 can be rounded and an opposite end can be substantially flat. As also shown in FIGS. 16-22, the outer prong 404 can include an outer base 424 and an outer posts 405A and 405B. The outer base 424 can have substantially flat inner and/or outer surfaces. At least one end of the outer base 424 can be rounded and/or squared. As shown in FIG. 16, one end of the outer base 424 can be rounded and an opposite end can be substantially flat.

The inner post 403 can extend from the inner base 422. For example, the inner post 403 can be positioned on one side of the joint 421. A portion of the inner prong 402 can be inserted into a patient's nose. For example, the inner post 403 can be inserted into a patient's nose to be secured to the inner surface of the patient's nose while the inner base 422 of the inner prong 402 can lie outside or substantially outside a patient's nose. Alternatively, a portion of the inner prong 402 can be secured to an outside portion of a patient's nose when the nose sensor 400 is in use.

The outer prong 404 can be approximately parallel to the inner prong 402. This can help to maintain an alignment between the emitter and/or the detector in use, as described above.

The inner post 403 can be positioned approximately at a center region of an end or surface of the inner base 422. As shown in FIGS. 16-22, at least a portion of the outer prong 404 and/or the inner prong 402 can be curved. For example, at least the inner post 403 and the outer posts 405A, 405B can be curved. The curvature of the inner post 403 and/or the outer posts 405A, 405B can help to conform to the shape of the patient's nose, as discussed with respect to the nose sensor 200, 300 previously. This can help to accommodate a variety of nasal geometries and/or can be more comfortable to the user. The outer prong 404 and/or the inner prong 402 can be generally straight such that the outer and inner prongs 404, 402 extend outwardly from the coupling portion 420.

The inner post 403, the inner base 422, and/or the joint portion 421A can be integrally formed. Alternatively, the inner post 403, the inner base 422, and/or the joint portion 421A can be not integrally formed, but rather, can be secured or connected to one another prior to assembly of the nose sensor 400. For example, the inner post 403, the inner base 422, and/or the joint portion 421A can be adhered or bonded to one another.

The outer posts 405A, 405B, and/or 405C, the outer base 424, and/or the joint portion 421B can be integrally formed. Alternatively, the outer posts 405A, 405B, and/or 405C, the outer base 424, and/or the joint portion 421B can be not integrally formed, but rather, can be secured or connected to one another prior to assembly of the nose sensor 400. For example, the outer posts 405A, 405B, and/or 405C, the outer base 424, and/or the joint portion 421B can be adhered or bonded to one another.

The inner prong 402 and the outer prong 404 can be secured to one another by a snap-fit connection. For example, instead of utilizing the joint 421 and pin 430, the inner prong 402 and the outer prong 404 could include a snap-fit connection whereby the inner prong 402 and the outer prong 404 snap into place to secure to one another. This snap-fit connection could also be configured to allow rotation, such as rotation similar to the rotation permitted in the joint 421 configuration.

The inner post 403 can extend away from the coupling portion 420 in a first and/or second direction. The inner prong 302 can include a detector coupled to the inner post 303 as described in more detail below. At least a portion of the inner prong 402 can be configured to be positioned within a patient's nose. At least a portion of the inner prong 402 can be positioned adjacent an inner surface of a patient's nose. At least a portion of the inner prong 402 can engage at least a portion of an inner surface of a patient's nose. At least a portion of the inner prong 402 can be positioned within a patient's nose and/or at least a portion of the inner prong 402 can remain outside of the patient's nose when the nose sensor 400 is in use. Alternatively, at least a portion of the inner prong 402 can be configured to be positioned outside a patient's nose. At least a portion of the inner prong 402 can be positioned adjacent an outer surface of a patient's nose. At least a portion of the inner prong 402 can engage at least a portion of an outer surface of a patient's nose.

The inner prong 402 can include at least one inner post 403. The inner post 403 can be coupled with the detector as discussed in more detail below. Thus, the inner post 403 can be configured to be positioned within the patient's nose, as discussed above. Alternatively, the inner post 403 can be configured to be positioned along an exterior portion of a patient's nose.

The outer prong 404 and/or the inner prong 402 can comprise various lengths. The outer posts 405A, 405B, and/or 405C of the outer prong 404 can be longer than the inner post 403 of the inner prong 202. The outer posts 405A, 405B, and/or 405C of the outer prong 404 can be shorter than the inner post 403 of the inner prong 202. Thus, the outer posts 405A, 405B, and/or 405C of the outer prong 404 and the inner post 403 of the inner prong 202 can comprise various lengths so as to aid securement to patient's having varying sizes and/or shapes of noses. The outer posts 405A, 405B, and/or 405C of the outer prong 404 and the inner post 403 of the inner prong 402 can comprise various lengths so as to aid comfort to patient's having varying sizes and/or shapes of noses when the nose sensor 400 or a portion thereof is attached to the patient.

The outer posts 405A, 405B, 405C, the inner post 403, and/or the inner post 405C, can comprise a cross-section that is circular. Alternatively, the outer posts 405A, 405B, 405C, the inner post 403, and/or the inner post 405C can comprise a cross-section that is non-circular. For example, the outer posts 405A, 405B, 405C, the inner post 403, and/or the inner post 405C can comprise a cross-section that is polygonal. The outer posts 405A, 405B, 405C, the inner post 403, and/or the inner post 405C can comprise a cross-section that is triangle, quadrilateral, pentagonal, hexagonal, heptagonal, octagonal, nonagonal, decagonal, or otherwise shaped. The outer posts 405A, 405B, 405C, the inner post 403, and/or the inner post 405C can comprise a cross-section that is some combination of these circular and/or polygonal shapes. For example, the outer posts 405A, 405B, 405C, the inner post 403, and/or the inner post 405C can comprise a cross-section that is partially circular and partially polygonal.

As shown in FIG. 16, for example, the outer posts 405A, 405B, and/or 405C can be curved towards the inner prong 402 and/or inner post 403. Alternatively, the outer posts 405A, 405B, and/or 405C can be generally straight such that the outer posts 405A, 405B, and/or 405C extend generally upwardly from the coupling portion 420 and/or the outer base 424. The shape of the outer prong 204 and/or outer posts 405A, 405B, 405C can beneficially help to secure the nose sensor 400 to the patient's nose. For example, the shape of the outer prong 204 relative to the shape of the inner prong 202 can help to secure the nose sensor 200 to the patient's nose. As shown in FIG. 16, for example, an intermediate portion of the inner post 403 of the inner prong 202 and an intermediate portion of the outer posts 405A, 405B of the outer prong 204 are curved in a similar direction and at a similar radius of curvature to one another to help to secure the nose sensor 400 to the patient's nose in use.

Figure 21:
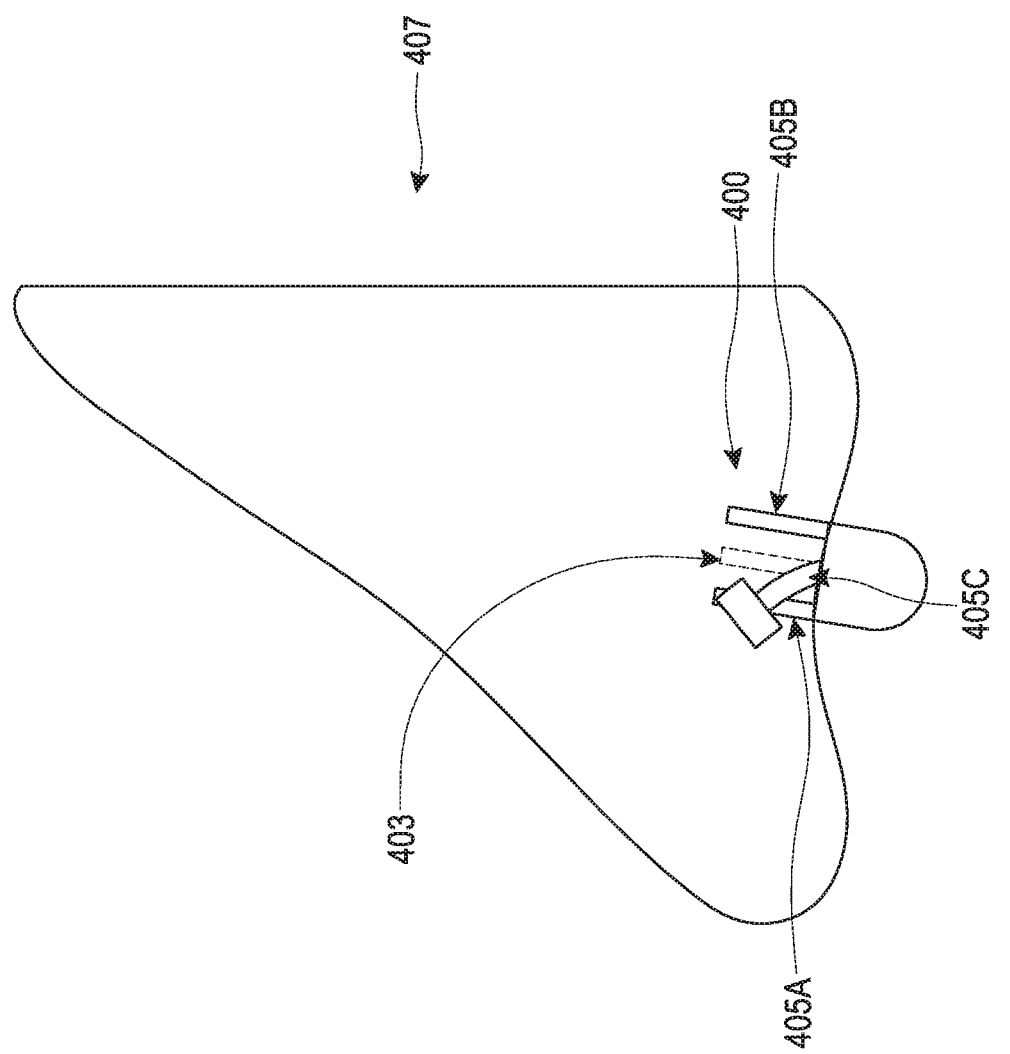
FIG. 21 illustrates a perspective view of the nose sensor of FIG. 16 in use.
Figure 22:
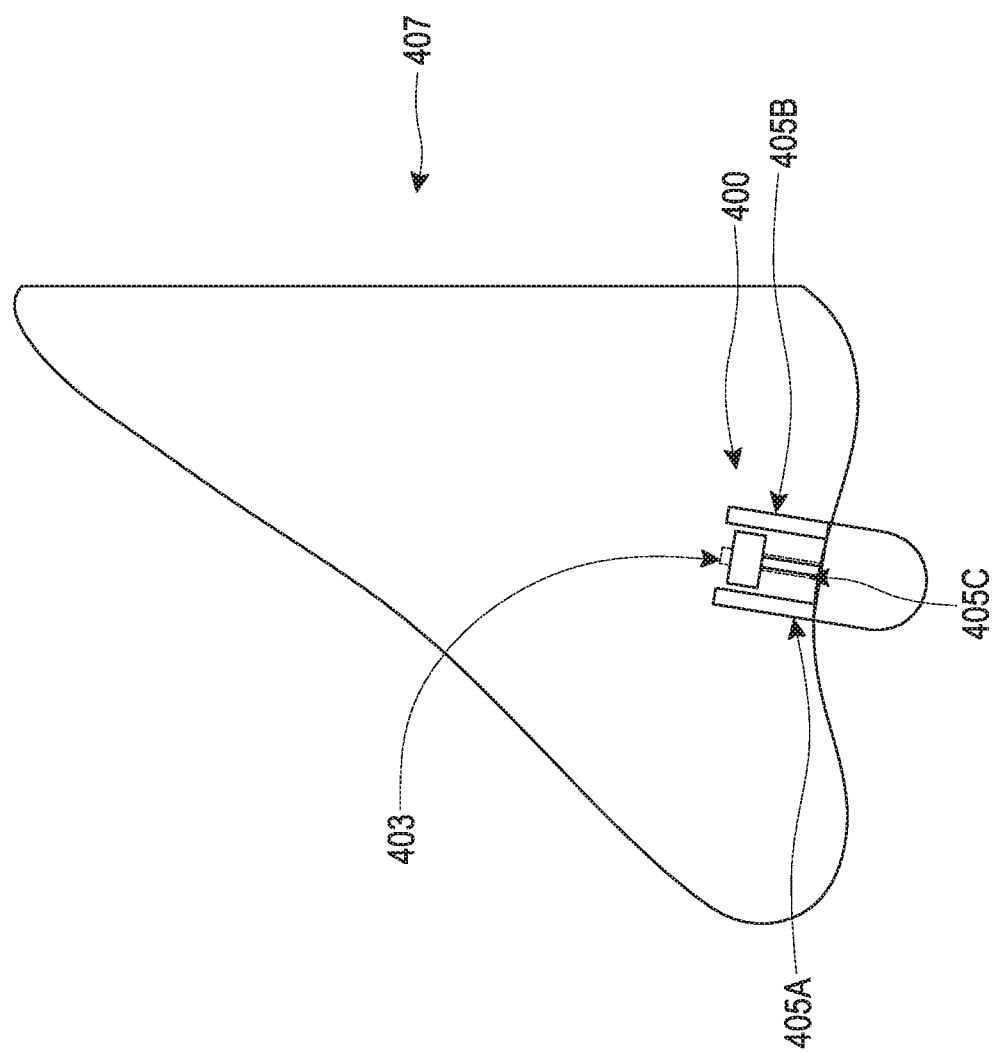
FIG. 22 illustrates a perspective view of the nose sensor of FIG. 16 in use.

FIGS. 21 and 22 illustrate the nose sensor 400 when secured to a patient's nose. As shown, at least a portion of the inner post 403 can slide into the patient's nose and engage an inner surface of the patient's nose. At least a portion of the outer posts 405A, 405B, 405C can slide along an outer region of the patient's nose and engage an outer surface of the patient's nose. Alternatively, at least a portion of the inner post 403 can slide along an outer region of the patient's nose and engage an outer surface of the patient's nose, and at least a portion of the outer posts 405A, 405B, 405C can slide into the patient's nose and engage an inner surface of the patient's nose. These configurations can help to ensure that the nose sensor 400 remains secured to the patient's nose and/or is comfortable when secured to the patient. These configurations can help to allow the nose sensor 400 to sit flush against the patient's tissue, inside and/or outside of the patient's nose. The sensor 400 may be less bulky and/or occupy less space on the patient's tissue.

Figure 18:
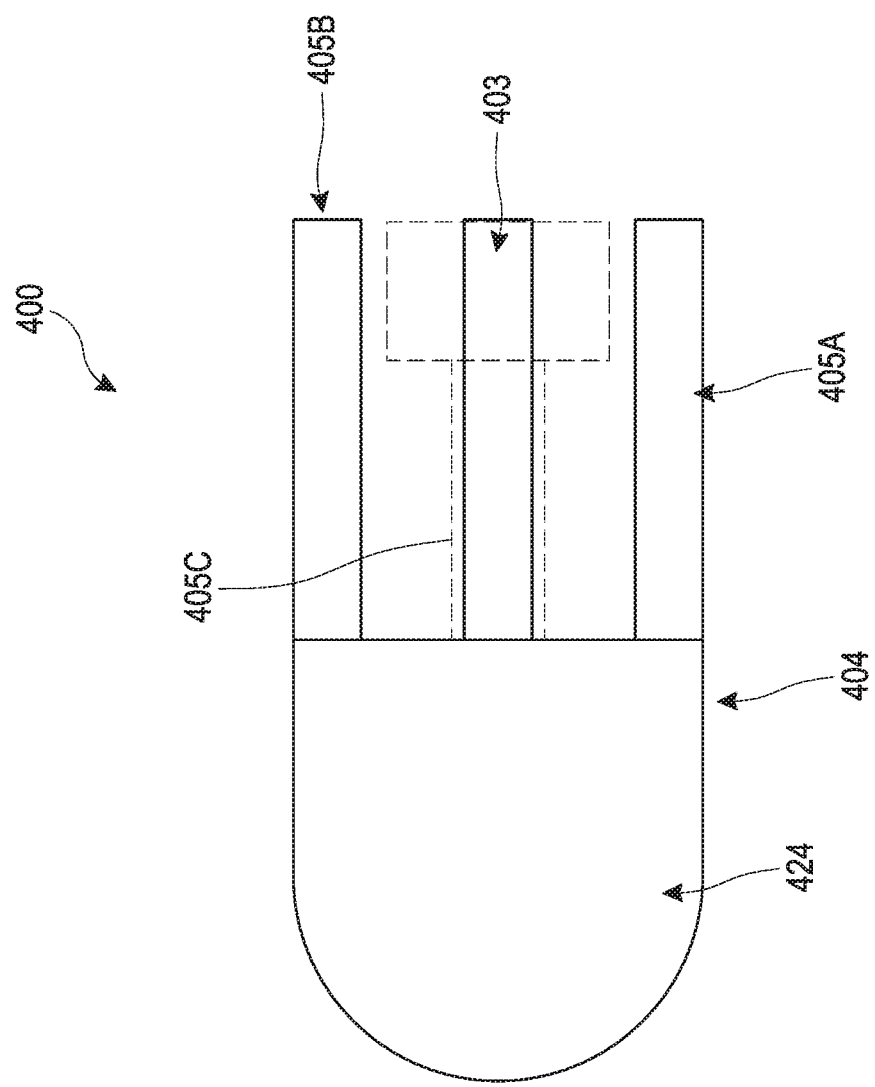
FIG. 18 illustrates a perspective view of the nose sensor of FIG. 16.
Figure 19:
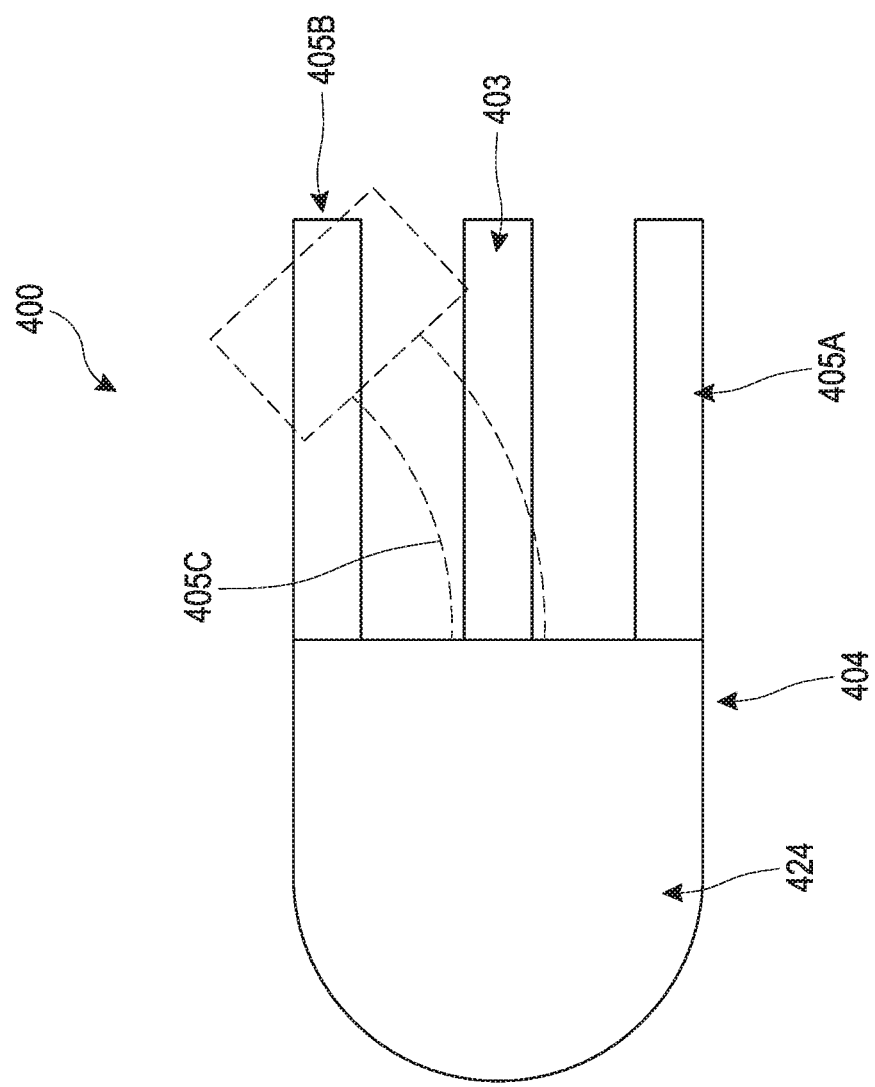
FIG. 19 illustrates a perspective view of the nose sensor of FIG. 16.
Figure 20:
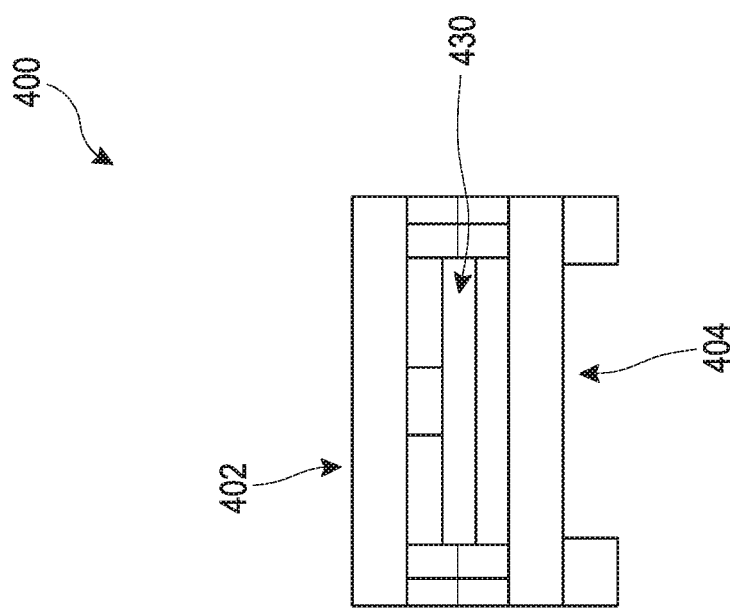
FIG. 20 illustrates a perspective view of the nose sensor of FIG. 16.

As shown in at least FIG. 18, a central longitudinal axis of the inner post 403 can be aligned with or parallel to a central longitudinal axis of the inner prong 402. As also shown in FIG. 18, a central longitudinal axis of the inner post 403 can be aligned with a central longitudinal axis of the outer post 405C, which can help ensure that the emitter and the detector are aligned to accurately measure physiological parameters when the nose sensor 400 is in use. The outer post 405A can be spaced from the outer post 405B.

As shown, the outer prong 404 can include outer posts 405A, 405B and an outer base 424. The outer base 424 can be coupled to and/or formed with the coupling portion 420 at one side and to the outer posts 405A, 405B at another side. The outer posts 405A, 405B can be spaced apart along a portion of the outer base 424. For example, the outer posts 405A, 405B can be spaced apart along a top portion of the outer base 424. As shown, the inner post 403 can be positioned between the outer posts 405A, 405B in a top view of the nose sensor 400 (for example, as shown in FIG. 18).

As illustrated in at least FIGS. 16 and 18, the inner post 403 can include a first side wall and a second side wall. The outer post 405A and/or the outer post 405B can be spaced laterally away from one another along the outer prong 404 and/or the outer base 424. The outer post 405A can be positioned laterally outward from the first side wall of the inner post 403. The outer post 405B can be positioned laterally outward from the second side wall of the inner post 403.

The inner post 403 can apply pressure to an inner portion of the nose of the patient when the nose sensor 400 is secured to at least a portion of the patient's nose. The outer post 405A can apply pressure to a portion of the nose of the patient that can be spaced laterally outwardly from at least a portion of the inner portion of the patient's nose where the inner post 403 applies a pressure when the nose sensor 400 is secured to the patient. The outer post 405B can apply pressure to a portion of the nose of the patient that can be spaced laterally outwardly from the inner portion of the patient's nose where the inner post 403 applies a pressure when the nose sensor 400 is secured to the patient. The inner post 403 can apply pressure to a portion of the nose of the patient, as discussed above. The portion of the nose of the patient can be positioned between the outer post 405A and/or the outer post 405B when the inner prong 402 and the outer prong 404 of the nose sensor 400 are secured to the patient. The inner post 403 of the inner prong 402 can apply pressure to a portion of the nose of the patient. The portion of the nose of the patient can be positioned between the outer post 405A and the outer post 405B when the inner prong 402 and the outer prong 404 are secured to the patient.

To secure the nose sensor 400 to the patient, the inner post 403 can apply pressure to an inner surface of the patient's nose, as discussed above. For example, the inner post 403 can apply pressure from the inside of the patient's nose towards the outside of the patient's nose. The outer post 405A and/or the second outer post 405B can apply pressure to the outer surface of the patient's nose. For example, the outer post 205A and/or the outer post 405B can apply pressure from the outside of the patient's nose towards the inside of the patient's nose. The inner post 403 can apply pressure to a portion of the patient's nose that is positioned at least partially between the outer posts 405A, 405B. The outer posts 405A, 405B can apply pressure to a portion of the patient's nose that is positioned at least partially outwardly from the inner post 403.

As discussed above, the positioning of the inner prong 402 and/or the outer prong 404 of the nose sensor 400 can advantageously help to secure the nose sensor 400 to the patient while also minimizing the contact of portions of the nose sensor 400 with the patient. As also discussed above, varying the positioning of portions of the nose sensor 400 and/or minimizing the contact between portions of the nose sensor 400 and the patient can aid patient comfort and improve securement. For example, the inner prong 402 (or portions thereof), the outer prong 404 (or portions thereof), and/or the coupling portion 420 can secure to the patient by contacting one or more points, areas, or portions of the patient's nose. For example, the inner prong 402 can contact an inner or outer portion of the patient's nose and the outer posts 405A, 405B of the outer prong 404 can contact a different inner or outer portion of the patient's nose when the nose sensor 400 is secured to the patient. Compared to other sensors which may contact a larger portion or region of a patient's nose when secured to the patient, the configuration of the inner prong 402 and/or outer prong 404 of the nose sensor 400 can contact less of a portion or region of a patient's nose when the nose sensor 400 is secured to a patient. As discussed above, the inner prong 402 and/or outer prong 404 of the nose sensor 400 can be configured to contact a minimal amount of a portion or region of a patient's nose when the nose sensor 400 is secured to a patient.

The nose sensor 400 can measure various physiological parameters of a patient, as discussed above. Similar to nose sensor 200 and/or 300, the nose sensor 400 can include an emitter and a detector to allow the nose sensor 400 to measure the patient's physiological parameters, such as those discussed herein.

Various arrangements of the emitter and/or the detector can allow the nose sensor 400 to take more accurate measurements. The emitter can be a light-emitting diode (LED). The emitter can emit light of a certain wavelength. The light emitter can emit light of different wavelengths in sequence with only one emitter emitting light at a given time, thereby forming a pulse sequence. The number of emitters is not limiting and can range from two to eight, or more in some instances. Detailed descriptions and additional examples of the light emitters are provided in U.S. Pat. No. 9,277,880, referenced above.

The detector can detect light from the emitter after the light passes through and is attenuated by tissue of the patient's nose. For example, the detector can comprise photodetectors, photodiodes, phototransistors, and/or the like. Additional details of the photodetector are described in U.S. Pat. No. 9,277,880, referenced above. The detector can generate an electrical signal based on the detected light from the emitter. The signal of the detected light from the emitter can be input into a signal processor described herein, such that the signal processor can process an output of the sensor 400.

The detector of nose sensor 400 can be positioned along the inner prong 402. For example, the detector can be coupled with an end of the inner post 403 of the inner prong 202, similar to nose sensor 200 and/or 300. The detector can be coupled with an upper edge of the inner post 403. The detector can be coupled with an inner surface of the inner post 403. The detector can be adhered, bonded, formed into, and/or otherwise attached to the inner post 403. The detector can be configured to connect to the inner post 403 by a snap-fit connection. The inner post 403 and the detector can be integrally formed. The detector can be secured to an inner surface of the patient's tissue within the patient's nose. The detector and/or the emitter can advantageously assist in desensitizing the nose sensor 400 to various geometric variations.

The detector can be secured to the inner surface of the patient's nose by an adhesive. Alternatively, the detector can be secured to the inner surface of the patient's nose without adhesives. For example, the engagement of the outer prong 404 and/or the inner prong 402 with the patient's nose can hold the detector against the inner surface of the patient's nose without the use of adhesives.

The detector can be secured to the outer surface of the patient's nose by an adhesive. Alternatively, the detector can be secured to the outer surface of the patient's nose without adhesives. For example, the engagement of the outer prong 404 and/or the inner prong 402 with the patient's nose can hold the detector against the outer surface of the patient's nose without the use of adhesives.

The emitter can be secured to the inner surface of the patient's nose by an adhesive. Alternatively, the emitter can be secured to the inner surface of the patient's nose without adhesives. For example, the engagement of the outer prong 404 and/or the inner prong 402 with the patient's nose can hold the emitter against the inner surface of the patient's nose without the use of adhesives.

The emitter can be secured to the outer surface of the patient's nose by an adhesive. Alternatively, the emitter can be secured to the outer surface of the patient's nose without adhesives. For example, the engagement of the outer prong 404 and/or the inner prong 402 with the patient's nose can hold the emitter against the outer surface of the patient's nose without the use of adhesives. The emitter and/or the detector can include an adhesive layer and a release liner overtop the adhesive layer. The release liner can be removed when the emitter and/or the detector is ready to be secured to a patient's skins surface, such as an interior or exterior portion of a patient's nose.

The securement of the nose sensor 400 to the patient can be configured to maintain an alignment between the emitter and detector when the nose sensor 400 is in use, as discussed below. The detector can be angled away from the outer prong 404, the outer posts 405A, 405B, 405C and/or the emitter. The nose sensor 400 shape and/or size can be varied so as to reduce the bulkiness and/or the obtrusiveness of the nose sensor 400. Thus, the nose sensor 400 can maintain a generally low profile. The nose sensor 400 can include a diffuser positioned proximate to the emitter. For example, the diffuser can be positioned in front of the emitter. The diffuser can comprise silicone. For example, the diffuser can include white and/or black silicone to scatter a greater amount of light and/or more accurately measure a patient's physiological parameters. The diffuser can comprise materials other than silicone. For example, the diffuser can comprise acrylic and/or plastics such as polycarbonate and/or polycarbonate film or sheets. The diffuser can comprise glass such as opal glass, ground glass, patterned glass, and/or a combination of such materials. The diffuser can also comprise other materials with varying material properties and/or characteristics. The diffuser can comprise one or more layers with different material properties and/or characteristics. For example, the diffuser can comprise, two or more, three or more, four or more, five or more, six or more, seven or more, or eight or more layers with different material properties and/or characteristics. Additionally, the diffuser can comprise one or more layers with similar material properties and/or characteristics. For example, the diffuser can comprise, two or more, three or more, four or more, five or more, six or more, seven or more, or eight or more layers with similar material properties and/or characteristics.

The diffuser of the nose sensor 400 can diffuse emitted light prior to entering the tissue. The diffuser can advantageously spread out, disseminate, and/or scatter light exiting from the emitter into and/or around a portion of a patient's body, for example the nose. This can permit light originating from the emitter to pass through a wider region or area of a patient's body, and thus better facilitate collection of physiological parameters (such as those discussed above). The detector can be sized and shaped to receive the optical radiation after it attenuates through tissue and fluids of a portion of a body. Diffusing light prior to entering the tissue can be advantageous because the light is allowed to pass through more tissue. This allows the light to sample more of the body tissue before being detected. It also provides for more even and consistent light across a larger portion of tissue. The diffusion of light by the diffuser of the nose sensor 400 can be performed through a light diffusion layer on or proximate to the emitter structure.

The size and/or shape of the diffuser can help to avoid edge effects. For example, the thickness and/or diameter of the diffuser can help to avoid edge effects. Similarly, the proximity of the diffuser relative to the emitter can help to avoid edge effects. Such configurations can advantageously help to desensitize the nose sensor 400 to geometric variability. For example, the size and/or shape of the diffuser and/or the positioning of the diffuser can allow the nose sensor 400 to accommodate various nose shapes and/or sizes, and/or accurately measure a patient's physiological parameters when light is emitted from the emitter, diffused by the diffuser, transmitted through a portion of the patient's body, and detected by the detector.

As discussed above, the nose sensor 400 can include an emitter. The emitter can be coupled to outer post 405C of the outer prong 404. The outer post 405C can be formed or integral with the outer post 405A, the outer post 405B, and/or the outer prong 404. Alternatively, the outer post 405C can be separate from or not integral with the outer post 405A, the outer post 405B, and/or the outer prong 404. The outer post 405C can be configured to be inserted into a portion of the outer prong 404. For example, the outer post 405C can be inserted into an aperture (not shown) along the outer prong 404. The outer post 405C can be configured to be secured to the outer prong 404 or other portion of the nose sensor 400 via an adhesive, fastener, or another securement method. The outer post 405C can form a flap. The flap can be rigid or substantially rigid. Alternatively, the flap can be flexible. The flap can be flexible relative to the outer posts 405A, 405B, which can be substantially rigid. As shown in at least FIGS. 19 and 21, the flap can be pulled, bent, and/or peeled away from a patient's nose 407 in use. In use, the emitter can be secured to an outer surface of the patient's nose 407, as described below. Alternatively, in use, the emitter can be secured to an inner surface of the patient's nose 407. In some alternative configurations, the nose sensor 400 does not include an outer post 405C. For example, the nose sensor 400 can have an inner prong 402 including an inner post 403 and a detector, and an outer prong 404 with an outer post 405A, an outer post 405B, and a coupling portion 420. Such a configuration for a nose sensor 400 can be used alongside a separate emitter which can attach to an inside or outside portion of a patient's nose to interact with the detector of nose sensor 400. Such an emitter can be electronically coupled to the detector through wiring or a flexible circuit, as discussed herein.

As discussed above, the outer post 405C can form a flap. The emitter can be coupled with the flap. For example, the emitter can be coupled with an end of the flap. The emitter can be positioned on an inner and/or outer surface of the flap. The flap configuration can advantageously allow the nose sensor 400 to accommodate various nose geometries. For example, the flap can allow the emitter to be positioned approximately parallel to the detector in use. In use, the emitter can be positioned such that the emitter remains in alignment with the detector as the nose sensor 400 is attached to a patient. Thus, the emitter can remain in alignment with the detector regardless of the shape and/or size of the patient's nose. The outer post 405C can have a length that is different than the length of the inner post 403. For example, the outer post 405C can have a shorter length than the length of the inner post 403. Alternatively, the outer post 405C can have a greater length than the length of the inner post 403. A nose sensor 400 having an inner post 403 with a different length than the outer post 405C can allow an emitter coupled to the outer post 405C to be offset or not aligned with a detector coupled to the inner post 403. Such an offset can advantageously increase the path length between the emitter and the detector. For example, such an offset can advantageously allow for light emitted from the emitter to have to pass through more tissue before arriving and being detected by the detector. Even though misalignment between the emitter and the detector may result more scattering of light emitted from the emitter and less emitted light getting to the detector, the misalignment and resulting increase in path length can advantageously allow light to pass through more body tissue, which can result in more accurate measurement of physiological parameters.

The emitter and/or the detector can be spaced away from an intermediate region of the outer prong 404 and/or the inner prong 402, or other region of the inner prong 402 and/or the outer prong 404 that contacts the patient's tissue. This can help to space the measurement location, for example the space between the emitter and the detector, from the points, areas, and/or regions where the nose sensor 400 or portions thereof are secured to and/or contacting the patient. Spacing the measurement location from these securement locations can help to reduce false and/or inaccurate readings of physiological parameters such as those discussed herein. For example, a pressure region created by contact between the nose sensor 400 or portions thereof and the patient's tissue at and/or proximate to these securement locations may alter blood flow in the patient's tissue or otherwise affect the values of physiological parameters measured by the nose sensor 400. Thus, by spacing the emitter and/or the detector from points, areas, and/or regions where the nose sensor 400 or portions thereof are secured to and/or contacting the patient, the nose sensor 400 can allow for more accurate measurements of physiological parameters. As discussed above, the outer post 405C can be coupled with an emitter. The outer post 405C can be flexible. The outer post 405C can apply little or no pressure on a patient's nose when the outer post 405C and/or the emitter is secured to an inside or outside portion of a patient's nose. For example, the emitter can be coupled to the outer post 405C and the emitter can have an adhesive surrounding the emitter that helps secure the emitter and/or the outer post 405C to an inside or outside portion of a patient's nose. In such configuration, the outer post 405C and/or the emitter can advantageously apply little or no pressure to the patient's nose, which can allow for more accurate measurements of physiological parameters.

An open side of the emitter (for example, the side configured to face the patient's tissue) can be secured to and/or positioned against an outside surface of the patient's nose. The emitter and/or the detector can be secured to the patient's nose before, during, and/or after securement of the outer prong 404 and/or the inner prong 402 to the patient's nose. The outer prong 404 and/or the inner prong 402 can be secured to the patient's nose before the emitter and/or the detector is secured to the patient's nose. For example, the emitter can be placed approximately aligned with the detector along an outer surface of the patient's nose 407. Alternatively, the emitter can be placed approximately aligned with the detector along an inner surface of the patient's nose 407.

The emitter can include an adhesive that can be configured to couple the emitter with the patient's nose. For example, the adhesive can secure the emitter to the patient's nose at a position approximately aligned with the detector. The emitter can include a liner. The liner can cover the emitter when the emitter is not in use. The liner can help to prevent the emitter from inadvertently adhering to another object. The liner can help to keep the emitter clean. The liner can help to maintain the adhesive properties of the adhesive backing of the emitter and prevent errant readings due to detection of light before the nose sensor 400 is in place. To secure the emitter to the patient, the liner can be removed.

The nose sensor 400 can include a lens on and/or around the detector. This lens can advantageously help focus light into the detector. For example, the lens can help focus light transmitted through a portion of a patient's body, such as a nose, and originating from the emitter. The lens can comprise various materials. For example, the lens can comprise glass and/or plastic. The lens can also comprise various optical refractive properties. For example, the lens can vary in thickness, curvature, refractive index, focal length, and/or other properties. The lens can be a simple lens. For example, the lens can comprise a single piece of transparent material. Alternatively, the lens can be a compound lens. For example, the lens can comprise one or more simple lenses arranged about a common axis. For example, the lens can comprise two or more, three or more, four or more, five or more, or six or more simple lenses arranged about a common axis. The lens can be paired with a diffuser to even out light distribution before detection and/or be surrounded by a black or dark colored border in order to block ambient stray light.

The nose sensor 400 can include wiring or a flexible circuit for electronically coupling the emitter and the detector. The nose sensor 400 can include wiring or a flexible circuit that couples the emitter and the detector and that is positioned within a portion of the nose sensor 400. For example, the nose sensor 400 can including wiring or a flexible circuit that connects to the emitter in an interior portion of the outer post 405C and that travels through an interior portion of the outer prong 404, passes up from the outer base 424 to the inner base 422 and travels through an interior of the inner prong 402 and/or the inner post 403 to connect to the detector. In such configurations, the wiring or flexible circuit can be configured to fit within interior portions of the outer prong 404, coupling portion 420, and/or inner post 403 of nose sensor 400. This can advantageously simplify the attachment and/or securement of the nose sensor 400. Alternatively, in some configurations, the wiring or flexible circuit can be configured to be outside of interior portions of the nose sensor 400. For example, the emitter can be electronically coupled to the detector by wiring or a flexible circuit that travels outside the nose sensor 400 or components of the nose sensor 400. The nose sensor 400 can have an emitter and no outer post 405C. For example, the nose sensor 400 can have a detector connected to a flexible circuit on one end of the flexible circuit and can have the other end of the flexible circuit connected to the emitter. In such configurations, the flexible circuit can connect to the detector at an end of the inner post 403, pass through an interior portion of the inner post 403, inner prong 402, inner base 422, outer base 424, and/or an opening in the outer prong 404 and connect to the emitter. Thus, a portion of the flexible circuit can be confined or secured within an interior portion of the nose sensor 400 and a portion of the flexible circuit connected to the emitter can be freely moveable outside the nose sensor 400 and can be secured to a portion of a patient's nose, such as an exterior portion.

Figure 17:
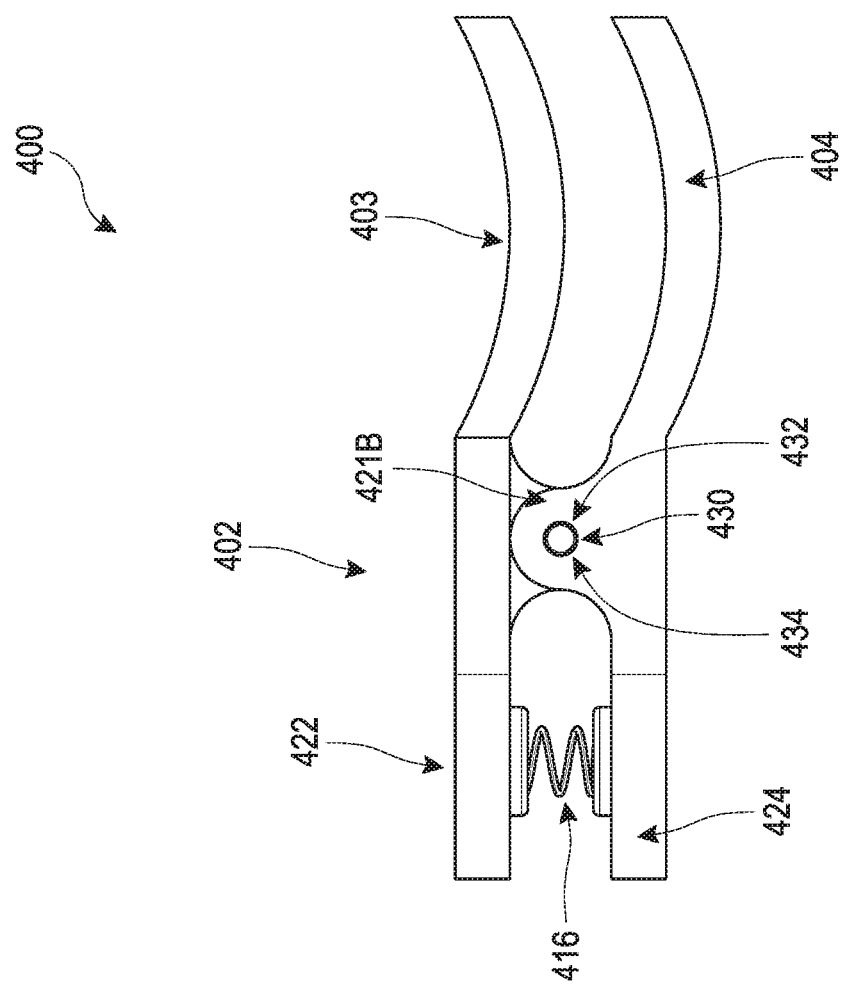
FIG. 17 illustrates a side view of the nose sensor of FIG. 16.

As shown by FIG. 17, the nose sensor 400 can include a biasing member 416. The biasing member 416 can include a spring, for example. The spring can comprise various strength and/or stiffness properties, and/or other material properties. The biasing member 416 can bias the outer prong 404 towards the inner prong 402 and/or the inner prong 402 towards the outer prong 404. The biasing member 416 can help to secure the nose sensor 400 to the patient. To attach the nose sensor 400 to the patient, a force can be applied to the inner base 422 and the outer base 424 such that the inner base 422 and the outer base 424 rotate about the pivot pin 430 towards one another. This can allow the nose sensor 400 to easily fit over the patient's nose. When no or minimal force is applied to the inner base 422 and/or the outer base 424, the nose sensor 400 can be secured to the patient's nose. The inner prong 402 can have a protruding rim that extends outward toward the outer prong 404. The inner prong 402 can have a recess configured to receive an end of the biasing member 416. The protruding rim and/or recess can help confine, align, and/or secure an end of the biasing member 416 to the inner prong 402. The outer prong 404 can have a protruding rim that extends outward toward the inner prong 402. The outer prong 404 can have a recess configured to receive an end of the biasing member 416. The protruding rim and/or recess can help confine, align, and/or secure an end of the biasing member 416 to the outer prong 404. The inner prong 402 and/or the outer prong 404 can include two or more protruding rims or skirts that can secure a portion of the biasing member 416. The inner prong 402 and/or the outer prong 404 can include two or more, three or more, four or more, five or more, or six or more protruding rims or skirts. For example, the inner prong 402 and/or the outer prong 404 can include two protruding rims along a surface portion of the inner prong 402 and/or the outer prong 404. The two protruding rims can permit a portion of the biasing member 416 to at least partially fit within, and the two protruding rims can secure the portion of the biasing member 416 by a snap-fit, press-fit, and/or friction fit. The biasing member 416 can be adhered to a surface of the inner prong 402 and/or a surface of the outer prong 404. This can help secure an end of the biasing member 416 to a surface of the inner prong 402 and/or a surface of the outer prong 404. The biasing member 416 can be cylindrical (see FIG. 17). Alternatively, the biasing member 416 can be non-cylindrical.

Figure 23:
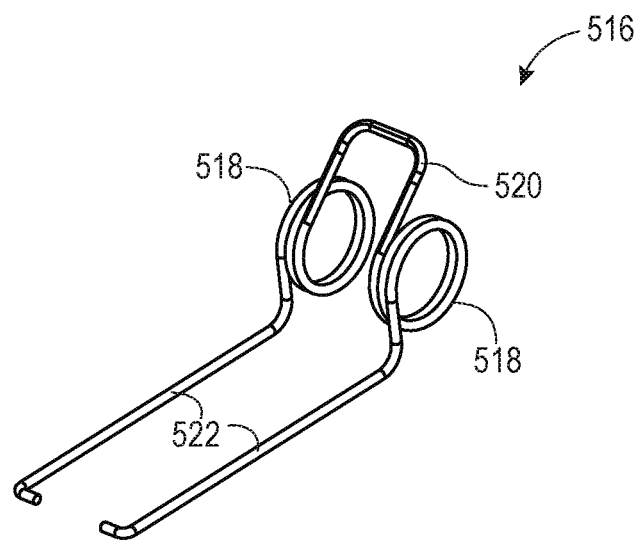
FIG. 23 illustrates a perspective view of a biasing member that can be incorporated into the nose sensor of FIG. 16.
Figure 24:
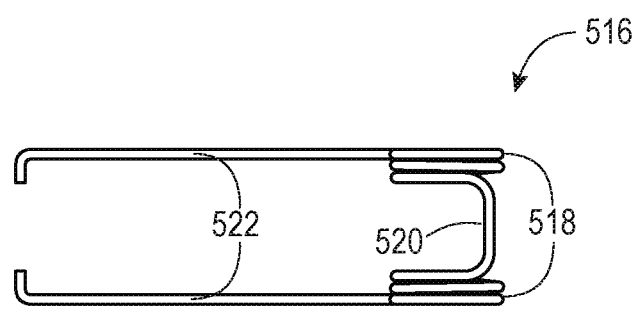
FIG. 24 illustrates a top view of a biasing member that can be incorporated into the nose sensor of FIG. 16.
Figure 25:
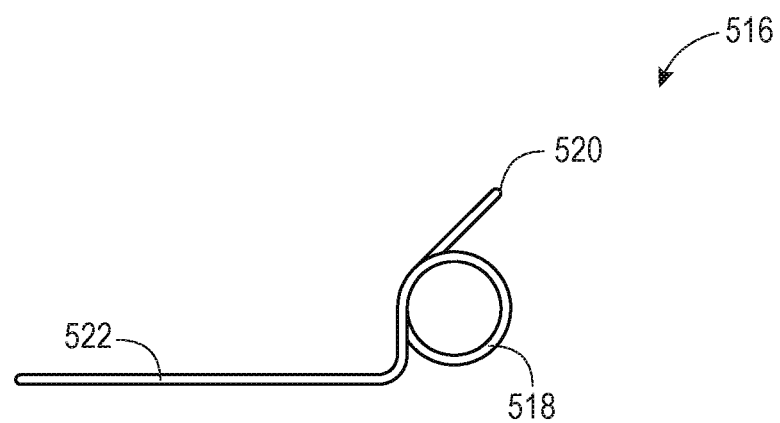
FIG. 25 illustrates a side view of a biasing member that can be incorporated into the nose sensor of FIG. 16.

FIGS. 23-25 illustrate an alternative biasing member 516 that can be incorporated into the nose sensor 400. The biasing member 516 can be a spring. The spring 516 can be configured to urge together and/or push apart the inner prong 402 and the outer prong 404. As shown in at least FIG. 17, the outer prong 404 can be rotatably connected to the inner prong 402 and/or the inner prong 402 can be rotatably connected to the outer prong 404. The spring 516 can be disposed between the inner prong 402 and the outer prong 404 and can be adapted to create a pivot point along a portion of a patient's nose that is gripped between the inner and outer prongs 402, 404. This advantageously allows the joint 421 to expand and/or retract so as to distribute force along the portion of the patient's nose that is secured to the sensor 400, comfortably keeping the portion in position without excessive force. The spring 516 can have coils 518, a first leg 520, and a second leg 522. The first leg 520 can press against the outer prong 404 or the inner prong 402. For example, when a portion of the nose sensor 400 is gripped, the first leg 520 can press against the outer or inner prong 404, 402. The second leg 522 can press against the outer prong 404 or the inner prong 402. For example, when a portion of the nose sensor 400 is gripped, second leg 522 can press against the outer or inner prong 404, 402. The inner prong 402 and/or the outer prong 404 can include recesses sized and shaped to fit at least a portion of the spring 516. For example, a portion of the first leg 520 can be configured to fit within a recess in the outer prong 404 to hold the first leg 520 in place. As another example, the second leg 522 can be configured to fit within a recess in the outer prong 404, or alternatively, the inner prong 402, to hold the second leg 522 in place. The inner prong 402 and/or the outer prong 404 can include protrusions sized and shaped to secure at least a portion of the spring 516. For example, a portion of the first leg 520 can be configured to fit between two protrusions or skirts that extend outward from a surface of the outer prong 404 or inner prong 402, thus holding the first leg 520 in place. As another example, For example, a portion of the second leg 522 can be configured to fit between two protrusions or skirts that extend outward from a surface of the outer prong 404 or inner prong 402, thus holding the second leg 522 in place. As shown in FIGS. 23-25, the first leg 520 can extend in an opposite direction as the second leg 522. Alternatively, the coils 518 of the spring 516 can be configured and/or wound so that the first leg 520 extends in the same direction as the second leg 522. The first leg 520 can extend so that it is parallel or substantially parallel to the second leg 522. Alternatively, the first leg 520 can extend so that it is non-parallel or perpendicular to the second leg 522.

Although this disclosure has been disclosed in the context of certain examples, it will be understood by those skilled in the art that the present disclosure extends beyond the specifically disclosed examples to other alternative examples and/or uses of the disclosure and obvious modifications and equivalents thereof. In addition, while a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the examples may be made and still fall within the scope of the disclosure. Accordingly, it should be understood that various features and aspects of the disclosure can be combined with or substituted for one another in order to form varying modes of the disclosed.

Features, materials, characteristics, or groups described in conjunction with a particular aspect, or example are to be understood to be applicable to any other aspect, or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing examples of systems. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that the actual steps taken in the processes illustrated and/or disclosed may differ from those shown in the figures. Depending on the system, certain of the steps described above may be removed, others may be added. Furthermore, the features and attributes of the specific examples disclosed above may be combined in different ways to form additional examples of systems, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular example. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain systems include, while other systems do not include, certain features, elements, and/or steps. Thus, such conditional language is not generally intended to imply that features, elements, and/or steps are in any way required for one or more systems or that one or more systems necessarily include logic for deciding, with or without user input or prompting, whether these features, elements, and/or steps are included or are to be performed in any particular system.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. Additionally, as used herein, "gradually" has its ordinary meaning (e.g., differs from a non-continuous, such as a step-like, change).

The scope of the present disclosure is not intended to be limited by the specific disclosures of the systems in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A noninvasive optical based physiological monitoring device comprising:
   an emitter configured to emit light of one or more wavelengths into tissue at a nasal measurement site of a user;
   a detector configured to detect at least a portion of the emitted light after attenuation through the tissue, the detected light usable to determine a physiological parameter;
   a first post configured to be positioned on one of an inner or outer side of the nasal measurement site of the user, the first post comprising a first end, a second end, and a length extending between the first and second ends, wherein the first post is curved along the length in a first direction about a first axis;
   a second post and a third post, the second and third posts spaced from one another and configured to be positioned on the other one of the inner or outer side of the nasal measurement site of the user, each of the second and third posts comprising a first end, a second end, and a length extending between the first and second ends of each of the second and third posts, wherein each of the second and third posts is curved along the length of each of the second and third posts in a second direction about a second axis, wherein the second axis is generally parallel to the first axis and wherein the first and second directions are the same;
   a coupling portion connected to and positioned at least partially between the first, second, and third posts, the coupling portion configured to position the first post away from both of the second and third posts to allow the noninvasive optical based physiological monitoring device to secure around a portion of the nasal measurement site of the user, wherein the emitter is coupled to the coupling portion, wherein the detector is positioned on the first post.

2. The noninvasive optical based physiological monitoring device of claim 1, wherein the first end of the first post is connected to the coupling portion, and wherein the detector is positioned on the second end of the first post.

3. The noninvasive optical based physiological monitoring device of claim 1, wherein the coupling portion comprises a first end connected to the first post, a second end connected to the second and third posts, and a length extending between the first and second ends of the coupling portion, wherein the coupling portion is curved along the length of the coupling portion.

4. The noninvasive optical based physiological monitoring device of claim 1, wherein the second and third posts form a generally U-shape along a plane extending between the second and third posts.

5. The noninvasive optical based physiological monitoring device of claim 1, wherein said physiological parameter is $SpO_2$.

6. The noninvasive optical based physiological monitoring device of claim 1, wherein said physiological parameter is pulse rate.

7. The noninvasive optical based physiological monitoring device of claim 1, further comprising a flexible flap connected to the coupling portion, wherein the emitter is positioned on the flexible flap.

8. A noninvasive optical based physiological monitoring device comprising:
   an emitter configured to emit light of one or more wavelengths into tissue at a nasal measurement site of a user;
   a detector configured to detect at least a portion of the emitted light after attenuation through the tissue, the detected light usable to determine a physiological parameter;
   a first post configured to be positioned on one of an inner or outer side of the nasal measurement site of the user, the first post comprising a first end, a second end, and a length extending between the first and second ends, wherein the first post is curved along the length in a first direction;
   a second post and a third post, the second and third posts spaced from one another and configured to be positioned on the other one of the inner or outer side of the nasal measurement site of the user, each of the second and third posts comprising a first end, a second end, and a length extending between the first and second ends of each of the second and third posts, wherein each of the second and third posts is curved along the length of each of the second and third posts in a second direction;
   a coupling portion connected to the first, second, and third posts, the coupling portion configured to position the first post away from both of the second and third posts, wherein the emitter is coupled to the coupling portion, and wherein the detector is positioned on the first post.

9. The noninvasive optical based physiological monitoring device of claim 8, wherein the first end of the first post is connected to the coupling portion, and wherein the detector is positioned on the second end of the first post.

10. The noninvasive optical based physiological monitoring device of claim 8, wherein the coupling portion comprises a first end connected to the first post, a second end connected to the second and third posts, and a length extending between the first and second ends of the coupling portion, wherein the coupling portion is curved along the length of the coupling portion.

11. The noninvasive optical based physiological monitoring device of claim 8, wherein the first and second directions are the same.

12. The noninvasive optical based physiological monitoring device of claim 8, wherein the first and second directions are different.

13. The noninvasive optical based physiological monitoring device of claim 8, wherein said physiological parameter is $SpO_2$.

14. The noninvasive optical based physiological monitoring device of claim 8, wherein said physiological parameter is pulse rate.

\* \* \* \* \*